US010213240B2

(12) United States Patent
Bryant et al.

(10) Patent No.: US 10,213,240 B2
(45) Date of Patent: Feb. 26, 2019

(54) DEPLOYABLE ANCHOR FOR BONE FIXATION

(71) Applicant: Cable Fix LLC, Hernando, MS (US)

(72) Inventors: Carey Bryant, Hernando, MS (US); Mark Brinker, Houston, TX (US); William Ricci, Richmond Heights, MO (US)

(73) Assignee: CABLE FIX LLC, Hernando, MS (US)

( * ) Notice: Subject to any disclaimer, the term of this patent is extended or adjusted under 35 U.S.C. 154(b) by 242 days.

(21) Appl. No.: 15/251,321

(22) Filed: Aug. 30, 2016

(65) Prior Publication Data

US 2018/0055550 A1     Mar. 1, 2018

(51) Int. Cl.
*A61B 17/86* (2006.01)
*A61B 17/04* (2006.01)
*A61B 17/68* (2006.01)
*A61B 17/88* (2006.01)

(52) U.S. Cl.
CPC ...... *A61B 17/8625* (2013.01); *A61B 17/0401* (2013.01); *A61B 17/8635* (2013.01); *A61B 17/683* (2013.01); *A61B 17/8665* (2013.01); *A61B 17/8685* (2013.01); *A61B 17/8869* (2013.01); *A61B 2017/0412* (2013.01); *A61B 2017/0424* (2013.01); *A61B 2017/681* (2013.01); *A61B 2017/8655* (2013.01)

(58) Field of Classification Search
CPC .................. A61B 17/0401; A61B 17/8625
See application file for complete search history.

(56) References Cited

U.S. PATENT DOCUMENTS

| 479,938 | A | | 8/1892 | Fredlihp |
|---|---|---|---|---|
| 899,612 | A | | 9/1908 | Phillips |
| 3,166,072 | A | | 1/1965 | Sullivan, Jr. |
| 4,060,089 | A | | 11/1977 | Noiles |
| 4,532,927 | A | | 8/1985 | Miksza, Jr. |
| 4,534,350 | A | | 8/1985 | Golden et al. |
| 4,534,352 | A | | 8/1985 | Korthoff |
| 4,548,202 | A | | 10/1985 | Duncan |
| 4,573,469 | A | | 3/1986 | Golden et al. |
| 4,610,250 | A | | 9/1986 | Green |
| 4,754,758 | A | | 7/1988 | Lehmann |
| 4,932,960 | A | | 6/1990 | Green |
| 5,358,510 | A | | 10/1994 | Luscombe et al. |
| 5,478,353 | A | | 12/1995 | Yoon |
| 5,620,452 | A | | 4/1997 | Yoon |
| 5,665,109 | A | | 9/1997 | Yoon |
| 5,797,932 | A | | 8/1998 | Min |
| 5,948,001 | A | * | 9/1999 | Larsen ............... A61B 17/0469 606/104 |
| 6,276,032 | B1 | | 8/2001 | Nortman et al. |
| 6,712,830 | B2 | | 3/2004 | Esplin |
| 6,966,919 | B2 | | 11/2005 | Sixto et al. |

(Continued)

*Primary Examiner* — Christian Sevilla
(74) *Attorney, Agent, or Firm* — Kunzler, PC

(57) ABSTRACT

Described herein is a deployable anchor that includes a head positionable within or entirely through an interior portion of a bone. While positioned within or entirely through the interior portion of the bone, the head is deployable to frictionally engage the bone and fixate the head relative to the bone. The anchor also includes a cable that is coupled to the head. The cable is configured to be tensioned to a measurable and adjustable tension.

28 Claims, 19 Drawing Sheets

(56) References Cited

U.S. PATENT DOCUMENTS

| | | |
|---|---|---|
| 7,033,378 B2 | 4/2006 | Smith et al. |
| 7,094,251 B2 | 8/2006 | Bonutti et al. |
| 7,678,122 B2 | 3/2010 | Kortenbach et al. |
| 7,854,750 B2 | 12/2010 | Bonutti et al. |
| 7,985,241 B2 | 7/2011 | Smith et al. |
| 8,080,020 B2 | 12/2011 | Kortenbach et al. |
| 8,114,100 B2 | 2/2012 | Smith et al. |
| 8,162,977 B2 | 4/2012 | Bonutti et al. |
| 8,454,628 B2 | 6/2013 | Smith et al. |
| 8,613,750 B2 | 12/2013 | Smith et al. |
| 9,039,596 B2 | 5/2015 | Sater |
| 9,220,503 B2 | 12/2015 | Ranchod |
| 9,788,827 B2 | 10/2017 | Miksza et al. |
| 2001/0051815 A1 | 12/2001 | Esplin |
| 2002/0029044 A1 | 3/2002 | Monassevitch et al. |
| 2004/0044366 A1 | 3/2004 | Bonutti et al. |
| 2004/0059349 A1 | 3/2004 | Sixto et al. |
| 2004/0059354 A1 | 3/2004 | Smith et al. |
| 2004/0059358 A1 | 3/2004 | Kortenbach et al. |
| 2007/0032825 A1 | 2/2007 | Bonutti et al. |
| 2008/0046007 A1 | 2/2008 | Schwemberger et al. |
| 2008/0046008 A1 | 2/2008 | Smith et al. |
| 2008/0108897 A1 | 5/2008 | Bonutti et al. |
| 2008/0140095 A1 | 6/2008 | Smith et al. |
| 2008/0147116 A1 | 6/2008 | Smith et al. |
| 2008/0149685 A1 | 6/2008 | Smith et al. |
| 2010/0179568 A1 | 7/2010 | Kortenbach et al. |
| 2010/0198258 A1* | 8/2010 | Heaven .............. A61B 17/0401 606/232 |
| 2011/0040307 A1 | 2/2011 | Ranchod |
| 2011/0092993 A1 | 4/2011 | Jacobs |
| 2011/0201877 A1 | 8/2011 | Sater |
| 2012/0130374 A1 | 5/2012 | Bouduban et al. |
| 2012/0143247 A1 | 6/2012 | Smith et al. |
| 2016/0081686 A1 | 3/2016 | Miksza et al. |
| 2016/0100835 A1 | 4/2016 | Linder et al. |
| 2016/0346023 A1 | 12/2016 | Bouduban et al. |
| 2017/0156738 A1 | 6/2017 | Ricci et al. |
| 2017/0156771 A1 | 6/2017 | Brinker et al. |
| 2017/0156772 A1 | 6/2017 | Brinker et al. |
| 2017/0156774 A1 | 6/2017 | Bryant et al. |
| 2017/0156775 A1 | 6/2017 | Bryant et al. |
| 2017/0156779 A1 | 6/2017 | Bryant et al. |
| 2017/0156847 A1 | 6/2017 | Ricci et al. |

* cited by examiner

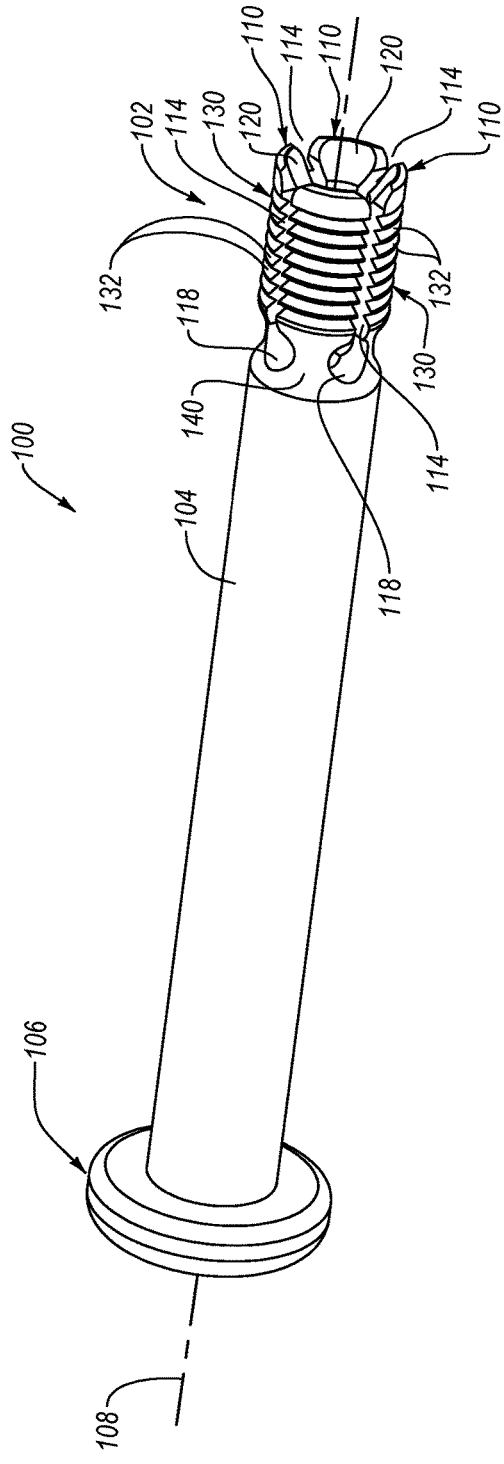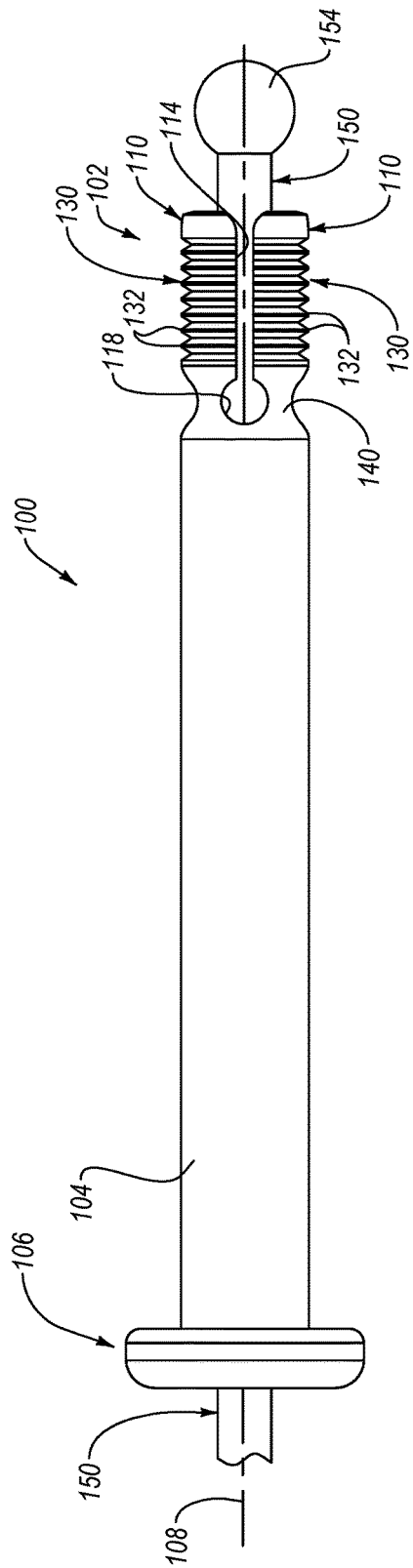

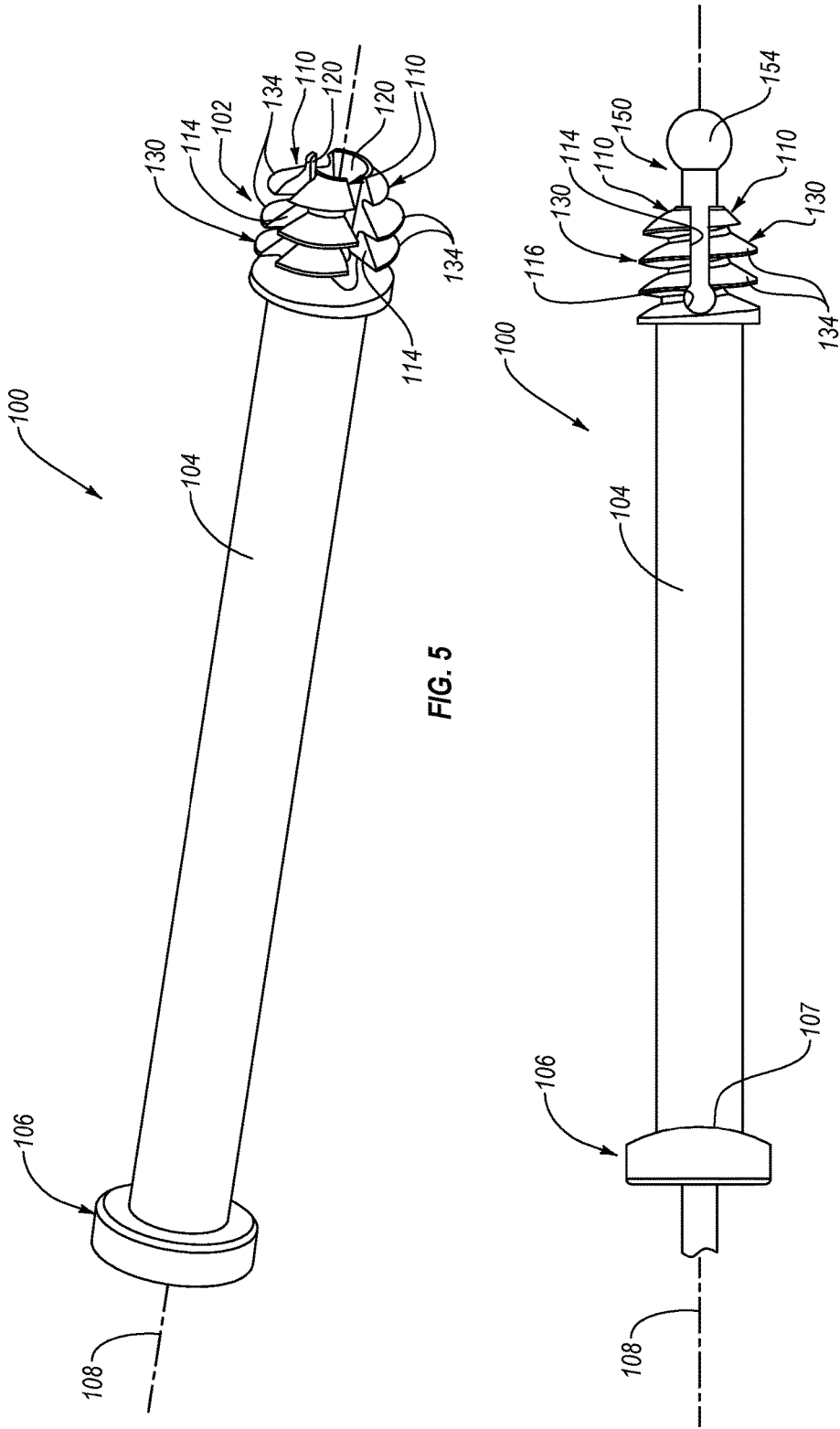

DEPLOYABLE ANCHOR FOR BONE FIXATION

FIELD

This disclosure relates generally to bone fixation and stabilization techniques and devices, and more particularly to an anchor that is deployable to engage a bone.

BACKGROUND

Various medical procedures utilize anchors to secure damaged skeletal tissue or soft tissue. Tissues, such as bone or soft-tissue, that have been fragmented, fractured, broken, torn, pulled, stretched, or otherwise damaged need to be set and held in specific orientations to properly heal. Anchors may be useful for securing/attaching various medical instruments, such as cables, sutures, and bone fixation devices, to a bone for the purpose of fixating bone fragments in place. For example, conventional anchors are positioned in a bone and the medical instruments are coupled to the anchors. These conventional anchors are non-deployable, such that once positioned in the bone, no portion of the anchors deploy.

SUMMARY

The subject matter of the present application provides embodiments of an anchor, mateable with a tensionable cable and deployable to engage a bone, that overcomes the above-discussed shortcomings of prior art anchors and techniques.

According to one embodiment, a deployable anchor, for bone fixation, includes a head that is positionable within or entirely through an interior portion of a bone. While positioned within or entirely through the interior portion of the bone, the head is deployable to frictionally engage the bone and fixate the head relative to the bone. The anchor also includes a cable that is coupled to the head. The cable is configured to be tensioned to a measurable and adjustable tension.

In some implementations of the anchor, the cable is coupled to the head such that tensioning of cable causes deployment of the head. The head may include at least two arms, each with bone engagement features. The cable can include an arm engagement portion, which causes the at least two arms to deform outwardly away from each other as the cable is tensioned.

According to certain implementations of the anchor, the head includes at least two arms separated by slits. Each of the at least two arms includes bone engagement features extending outwardly away from each other. Each of the at least two arms can include a tapered interior surface. The bone engagement features can include non-helical teeth, helical teeth, and/or a combination of non-helical teeth, helical teeth, or other bone engagement feature. In some implementations, the head does not include slits, and thus has a single annular arm on the head.

In certain implementations, the anchor further includes a washer that is fixedly coupled with the head. The anchor can additionally include an elongate shaft that extends between the washer and the head. Also, the anchor can include a central channel that extends entirely through the head and the washer. The cable can pass through the central channel.

According to some implementations of the anchor, a distance between the washer and the head is adjustable. The anchor may further include a telescoping element movably coupled with the elongate shaft. The washer is fixed to the telescoping element. The telescoping element is translationally movable relative to the elongate shaft to adjust the distance between the washer and the head. The anchor may additionally include a spring positioned within the elongate shaft between the telescoping element and the head.

In certain implementations, the anchor additionally includes bone engagement features between the washer and the elongate shaft. When the head is positioned within or entirely through the interior portion of the bone, the bone engagement features frictionally engage a near cortex of the bone and the head is deployable to frictionally engage a far cortex of the bone.

In some implementations, the anchor also includes external threads between the elongate shaft and the washer. The anchor may further include a compression nut threadably engaged with the external threads such that rotation of the compression nut relative to the external threads translationally moves the compression nut relative to the head.

According to some implementations of the anchor, movement of the cable along the central channel is constrained in a first direction and a second direction, opposite the first direction. The cable can include a plug positioned within the central channel when the cable passes through the central channel. The central channel may include a stop configured to contact and prevent movement of the plug relative to the central channel in the first direction. The anchor is insertable into the bone in the first direction and removable from the bone in the second direction.

According to yet another embodiment, a system for stabilizing a bone includes a deployable anchor and a tensioner. The anchor includes a head, positionable within or entirely through an interior portion of a bone and, while positioned within or entirely through the interior portion of the bone, deployable to frictionally engage the bone and fixate the head relative to the bone. Additionally, the anchor includes a cable coupled to the head. The cable is configured to be tensioned to a measurable and adjustable tension. The tensioner is configured to tension the cable to the measurable and adjustable tension.

In some implementations, the system further includes a fixation device that is positionable externally relative to the bone. The fixation device is fixable to the bone via engagement with the cable.

In certain implementations of the system, the deployable anchor further includes a washer fixedly coupled with the head, the fixation device includes a recess, and the washer is one of nestably engaged or threadably engaged with the recess of the fixation device.

According to yet another embodiment, a method of anchoring cable to bone includes positioning a head within or entirely through an interior portion of a bone and passing a cable through the head and coupling the cable to the head. The cable is configured to be tensioned to a measurable and adjustable tension. While the head is positioned within or entirely through the interior portion of the bone, the method includes deploying the head to frictionally engage the bone and fixate the head relative to the bone.

In some implementations, the method additionally includes tensioning the cable to the measurable and adjustable tension. Tensioning the cable deploys the head.

According to certain implementations of the method, the cable can include an arm engagement portion and the head can include at least two arms, each including bone engagement features. Deploying the head may include moving the arm engagement portion of the cable along the at least two arms, as the cable is tensioned, to deform the at least two arms outwardly away from each other. The method may additionally include crimping the cable, while tensioned to the measurable and adjustable tension, to maintain tension in the cable and deployment of the head.

In certain implementations, the method can also include positioning a washer, coupled to the head, proximate a first surface of the bone, where the interior portion of the bone is a near cortex of the bone that defines the first surface of the bone. Furthermore, the method can include positioning a fixation device external to the first surface of the bone, coupling the cable to the fixation device, and fixating the fixation device relative to the bone by tensioning the cable to the measurable and adjustable tension.

According to some implementations, the method further includes positioning a washer, coupled to the head, proximate a first surface of the bone. The interior portion of the bone is a far cortex of the bone that defines a second surface of the bone opposite the first surface of the bone. An elongate shaft extends between and couples together the head and the washer. The elongate shaft passes through a medullary cavity and a near cortex of the bone that defines the first surface of the bone.

According to another embodiment, a deployable anchor for bone fixation includes a head, positionable within or entirely through an interior portion of a bone and, while positioned within or entirely through the interior portion of the bone, deployable to frictionally engage the bone and fixate the head relative to the bone. The deployable anchor also includes a rod that is coupled to the head. The deployable anchor additionally includes a driver rotatably coupled with the rod. Totation of the driver relative to the rod moves the rod relative to the head and deploys the head.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter, they are not therefore to be considered to be limiting of its scope. The subject matter will be described and explained with additional specificity and detail through the use of the drawings, in which:

FIG. 1 is a perspective view of a deployable anchor, shown without a cable, according to one or more embodiments of the present disclosure;

FIG. 2 is a side elevation view of the deployable anchor of FIG. 1, shown with the cable, according to one or more embodiments of the present disclosure;

FIG. 5 is a perspective view of another deployable anchor, shown without a cable, according to one or more embodiments of the present disclosure;

FIG. 6 is a side elevation view of the deployable anchor of FIG. 5, shown with the cable, according to one or more embodiments of the present disclosure;

DETAILED DESCRIPTION

Figure 3:
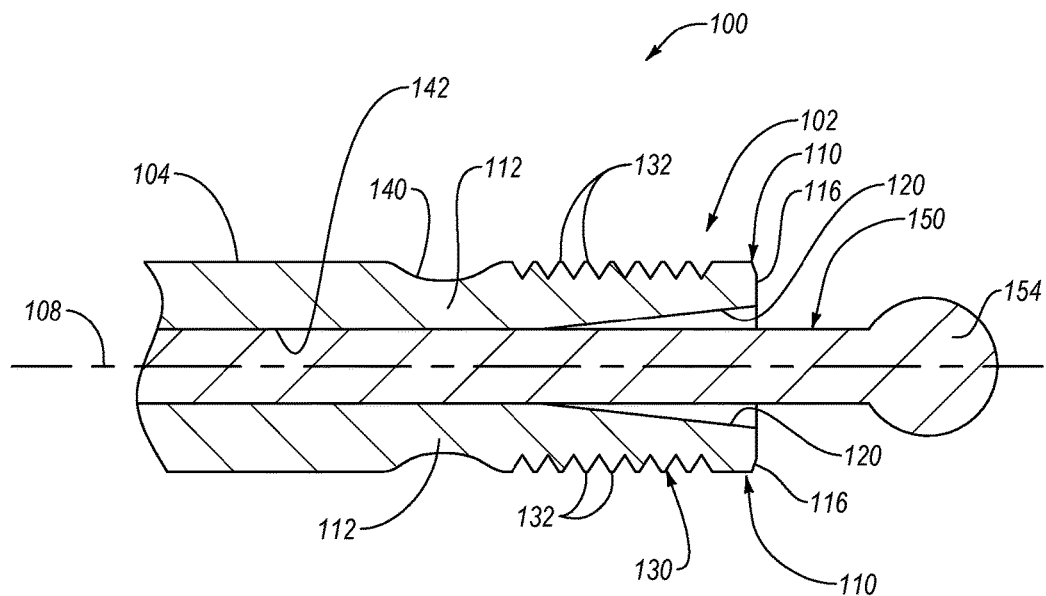
FIG. 3 is a cross-sectional side elevation view of a head of the deployable anchor of FIG. 2, shown with the head in a non-deployed state, according to one or more embodiments of the present disclosure.

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Referring to FIGS. 1 and 2, according to one embodiment, an anchor 100 includes a head 102, an elongate shaft 104, and a washer 106. The elongate shaft 104 extends between and couples together the head 102 and the washer 106. More specifically, the elongate shaft 104 positions the head 102 away from the washer 106 in a spaced-apart manner. As will be explained in more detail below, because of the elongate shaft 104, the anchor 100, shown in FIGS. 1 and 2, is defined as a bi-cortical anchor configured to extend, at least partially, through a bone from one side of the cortex of the bone (e.g., near cortex) to an opposing side of the cortex of the bone (e.g., far cortex).

Generally, the head 102 of the anchor 100 is configured to be deployable, when positioned within an interior portion (e.g., cortex or medullary cavity) of a bone or exteriorly of the bone after passing through the bone, to frictionally engage the interior portion of the bone or exterior surface of the bone and fixate the head 102, and thus the anchor 100, relative to the interior portion or exterior surface of the bone. Accordingly, the head 102 of the anchor 100 can have any of various features and configurations that facilitate the deployment of the head 102 and frictional engagement with the interior portion or exterior surface of the bone. In the illustrated implementations, head 102 includes a plurality of arms 110 extending longitudinally from the elongate shaft 104 along (e.g., parallel to) a central axis 108 of the anchor 100. The arms 110 are spaced-apart from each other by slits 114 extending longitudinally along the central axis 108. As defined by the slits 114, each arm 110 extends along the central axis 108 from an attached end 112 coupled to the elongate shaft 104 to a free end 116 (see, e.g., FIGS. 3 and 4). In this manner, each arm 110 is effectively cantilevered with respect to the elongate shaft 104. However, it is recognized that is some implementations, the head 102 does not include slits and multiple arms separated by the slits. Rather, in such implementations, the head 102 can be considered to have a single, annular, arm that deforms to mushroom outwardly as a single piece when the head 102 is deployed.

To facilitate deformation of the arms 110 at the attached ends 112, during deployment of the arms 110, the attached ends 112 may form a neck portion 140 of the head 102. The neck portion 140 has a reduced diameter relative to the elongate shaft 104. Accordingly, the thickness of the arms 110 at the attached ends 112 is reduced relative to the elongate shaft 104 and the arms 110 adjacent the neck portion 140. Due to the reduced thickness of the neck portion 140 at the attached ends 112 of the arms 110, the attached ends 112 of the arms 110 are more conducive to deformation and thus act as a deflection point about which the arms 110 deform and deflect when deployed. To further facilitate the predictable creation of a deflection point at the attached ends 112 of the arms 110, the head 102 may include cut-outs 118, as shown in FIGS. 1 and 2, formed in the attached ends 112 of the arms 110, such as in the neck portion 140 of the head 102, which are coextensive with the slits 114. In this manner, the thickness of the attached ends 112 is further reduced to more predictably create the deflection point at the attached ends 112 of the arms 110.

Figure 4:
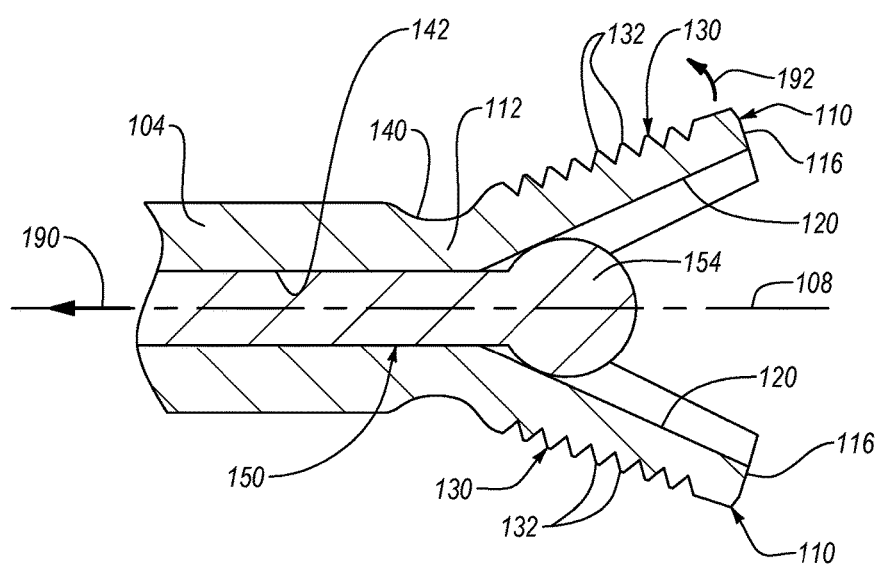
FIG. 4 is a cross-sectional side elevation view of the head of the deployable anchor of FIG. 2, shown with the head in a deployed state, according to one or more embodiments of the present disclosure.

As shown in FIGS. 3 and 4, the anchor 100 includes a channel 142 that extends the entirety of the length of the anchor 100. More specifically, the channel 142 extends through the head 102, elongate shaft 104, and washer 106. The portion of the channel 142 within the elongate shaft 104 and washer 106 is circumferentially enclosed and has a constant cross-sectional area in some implementations. However, in other implementations, the portion of the channel 142 within the elongate shaft 104 and washer 106 is only partially circumferentially enclosed and/or has a non-constant cross-sectional area. The portion of the channel 142 within the head 102 is not circumferentially enclosed, due to the slits 114, and does not have a constant-cross sectional area. More specifically, the arms 110 of the head 102 each has a tapered interior surface 120 such that the channel 142, within the head 102, diverges in a direction extending along the central axis 108 from the attached ends 112 of the arms 110 to the free ends 116 of the arms 110. As shown in FIG. 3, with the head 102 in a non-deployed state (e.g., the arms 110 have not been deployed), the cross-sectional area of the channel 142, along planes perpendicular to the central axis 108, increases from a minimum cross-sectional area at the attached ends 112 of the arms 110 to a maximum cross-sectional area at the free ends 116 of the arms 110. The maximum cross-sectional area at the free ends 116 of the arms 110 is sized to receive an arm engagement portion 154 of a cable 150. In some implementations, the maximum cross-sectional area at the free ends 116 of the arms 110 is equal to or larger than a maximum dimension (e.g., diameter) of the arm engagement portion 154 of the cable 150. However, in certain implementations, the maximum cross-sectional area at the free ends 116 of the arms 110 is smaller than a maximum dimension of the arm engagement portion 154 of the cable 150.

Each arm 110 includes bone engagement features 130 formed into an exterior surface of the arm 110 opposite the tapered interior surface 120. Generally, the bone engagement features 130 are configured to frictionally engage an interior portion of a bone. More specifically, the bone engagement features 130 are configured to frictionally engage the cortex of a bone. The bone engagement features 130 are designed to penetrate and grip the bone. Accordingly, in the illustrated embodiments, the bone engagement features 130 includes pointed ribs or teeth that, at least partially, cut or nest into the bone to frictionally engage the bone. The bone engagement features 130 are configured to induce a frictional engagement with the bone sufficient to withstand pull-out forces on the head, thus non-movably fixing or anchoring the head 102 relative to the bone.

According to the embodiment shown in FIGS. 1-4, the bone engagement features 130 include teeth 132. In the embodiment of FIGS. 1-4, the teeth 132 are non-helical, such that each of the teeth 132 defines a separate continuous annular tooth extending circumferentially about the exterior surface of a respective arm 110. In other words, the teeth 132 of an arm 110 are not co-joined, but each form an independent annular tooth. The heights of the points or peaks of each tooth 132 is constant circumferentially about the arms 110. Moreover, the teeth 132 on each arm 110 have the same height. Accordingly, in the non-deployed state, as shown in FIG. 3, the radial distance between the central axis 108 and the points or peaks of the teeth 132 are the same such that the points or peaks of the teeth 132 are co-planar with each other along planes parallel to the central axis 108.

Although the bone engagement features 130 shown in FIGS. 1-4 include multiple teeth 132, which are separate, continuous, and annular, positioned in a non-helical side-by-side manner, in other embodiments, the bone engagement features 130 can include teeth configured in a variety of other configurations or non-toothed engagement features configured in a variety of configurations that facilitate frictional engagement with a bone.

Still referring to FIGS. 2-4, the anchor 100 further includes the cable 150. As mentioned above, the cable 150 includes the arm engagement portion 154 situated at an end of the cable 150 and non-movably fixed relative to that end of the cable 150. The arm engagement portion 154 can be a generally bulbous element, such as a ball, wedge, etc., having a dimension greater than a maximum dimension of the cable 150. For example, in the illustrated embodiment, the arm engagement portion 154 is a ball with a diameter greater than a diameter of the cable 150. The arm engagement portion 154 can be non-movably fixed to the end of the cable 150 using any of various fixation techniques, such as co-forming the arm engagement portion 154 with the cable 150, swaging the arm engagement portion 154 onto the cable 150, crimping the arm engagement portion 154 onto the cable 150, or other like techniques.

As defined herein, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. In one embodiment, the measurable and adjustable tension may be a specific, known, predictable, expected, controllable, anticipated, desired, repeatable, sustainable, and/or predeterminable tension. For example, the cable 150 may be tensioned to a measurable and adjustable tension in order to facilitate the reduction and fixation of fractures or to otherwise facilitate the repair of dislocations or soft-tissue damage. In other words, the cable 150 is not a conventional suture or conventional thread material, since such materials are incapable of, or at least not well-suited for, maintaining a measurable and adjustable tension. Thus, the term "cable" can refer to a flexible, yet substantially non-stretchable, elongate cord-like element that can be tensioned to a measurable and adjustable tension. Because the cable 150 is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable 150 to be tensioned to a measurable and adjustable tension improves the reliability and reproducibility of surgical procedures when compared with other medical procedures that do not utilize cables. The cable 150 may be made from any one of various materials. For example, in specific implementations, the cable 150 is made from metal, such as stainless steel, titanium, or other metal.

The cable 150 is sized to be freely passed through the central channel 142 of the anchor 100. In contrast, the arm engagement portion 154 is sized to prevent free passage of the arm engagement portion 154 through the central channel 142. Accordingly, as shown in FIG. 3, in the non-deployed state, the cable 150 can be passed through and positioned within the central channel 142 of the anchor 100, while the arm engagement portion 154 is positioned outside or exteriorly of the central channel 142 proximate the free ends 116 of the arms 110.

Figure 12:
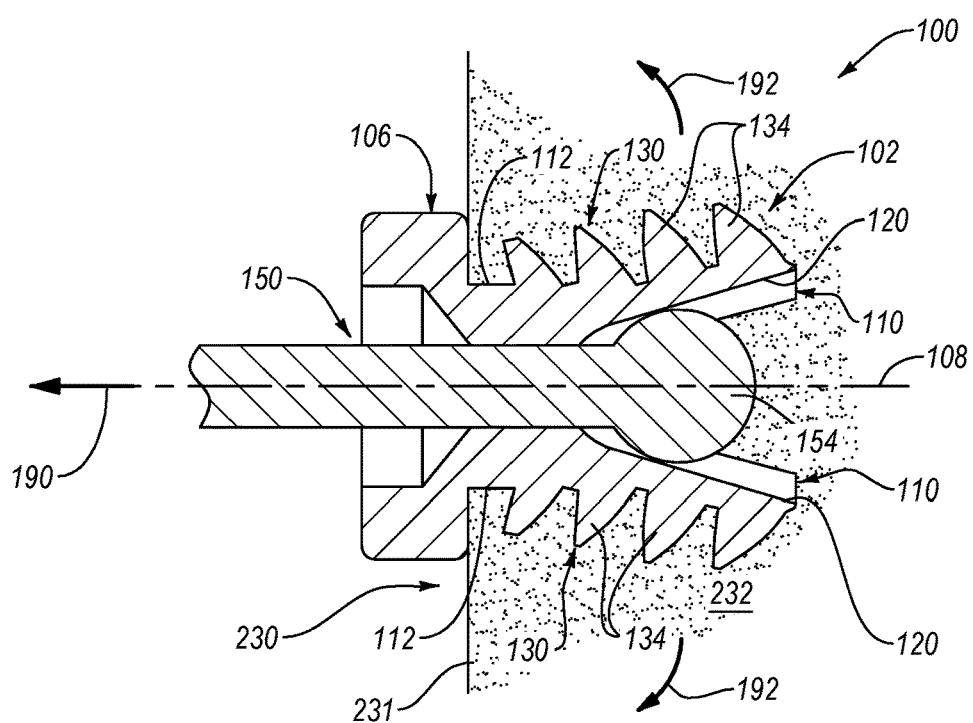
FIG. 12 is a cross-sectional side elevation view of the head of the deployable anchor of FIG. 10, shown with the head in a deployed state, according to one or more embodiments of the present disclosure.
Figure 13:
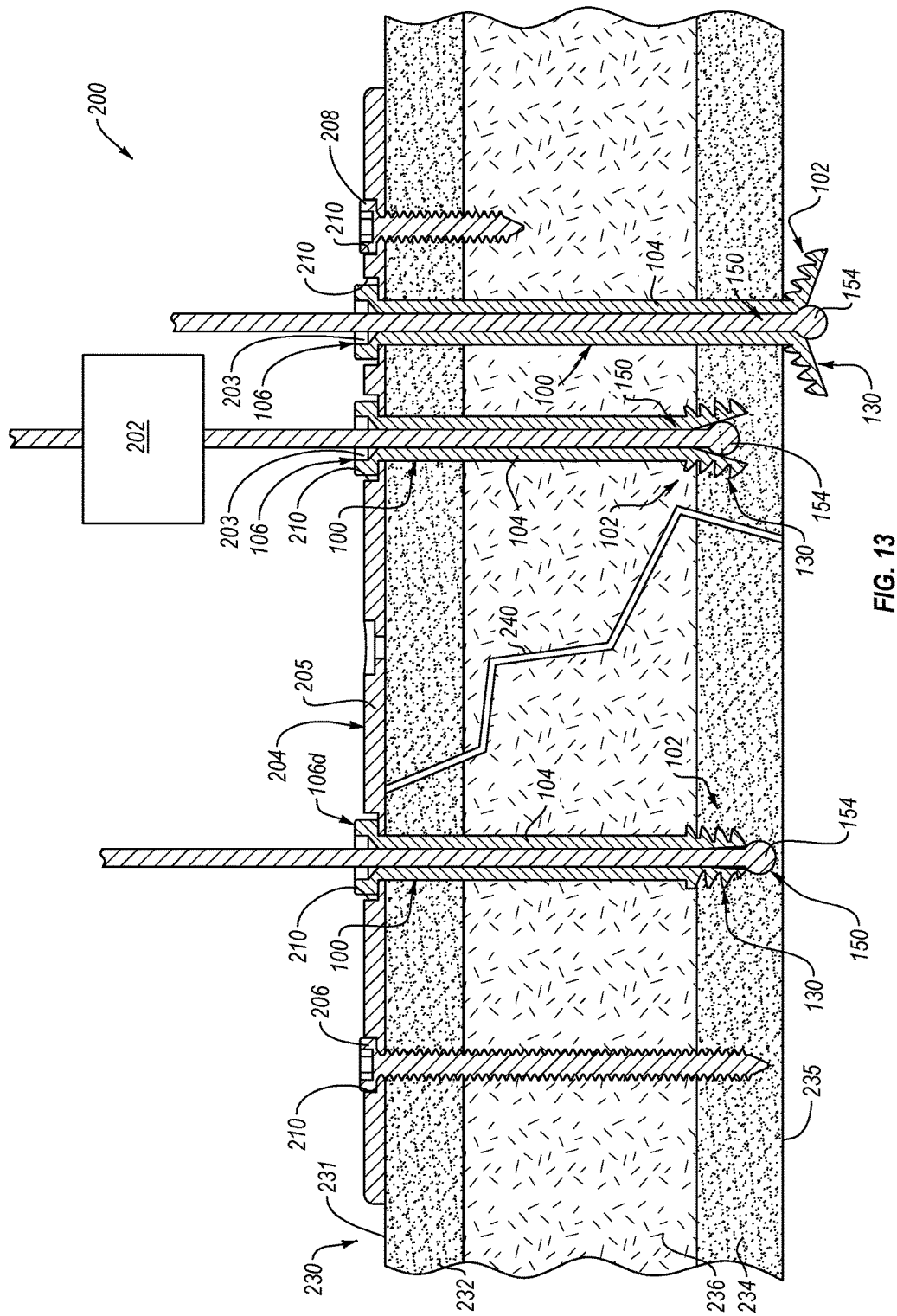
FIG. 13 is a cross-sectional side elevation view of a system for stabilizing a bone, according to one or more embodiments of the present disclosure.
Figure 14:
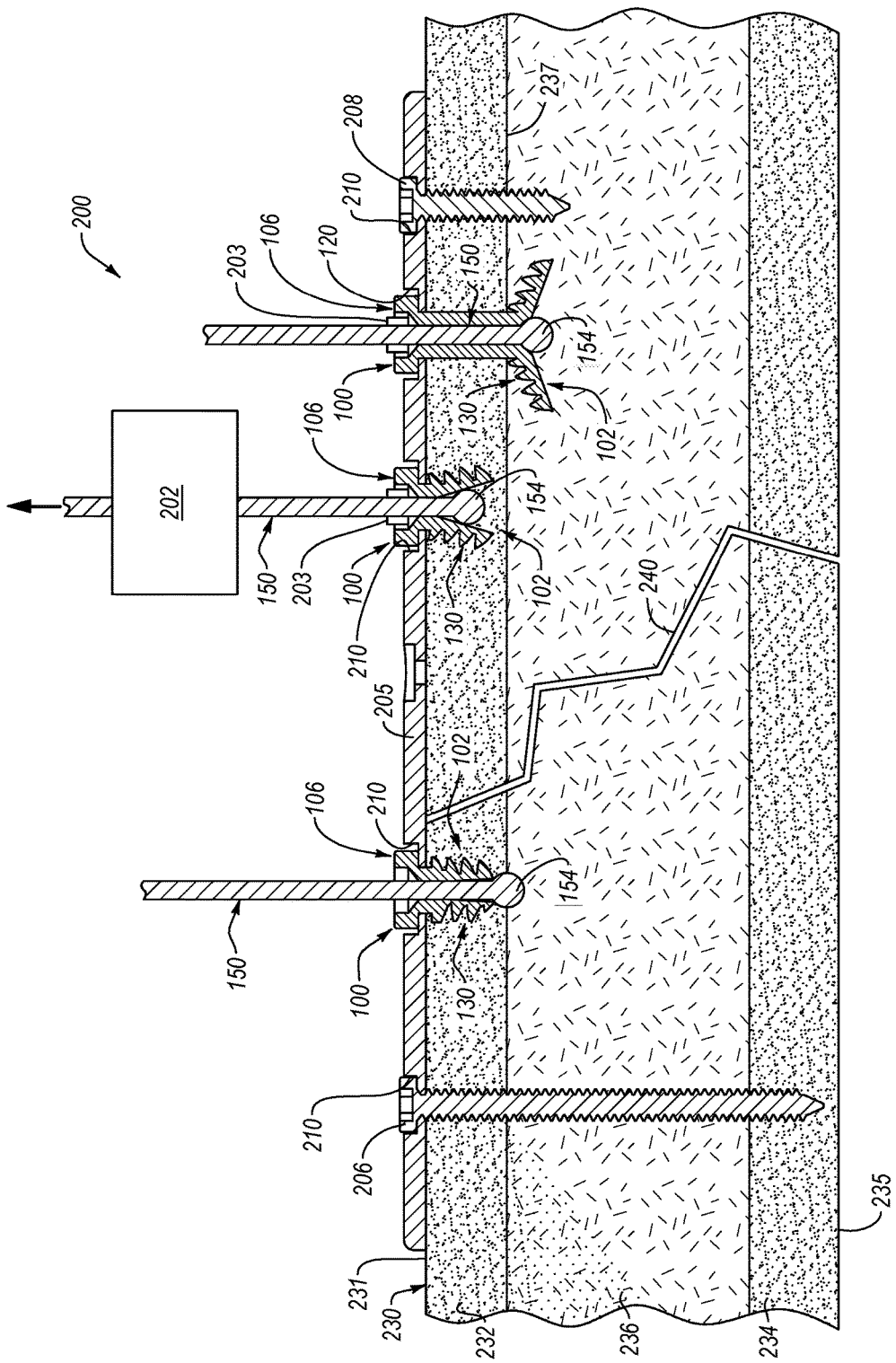
FIG. 14 is a cross-sectional side elevation view of another system for stabilizing a bone, according to one or more embodiments of the present disclosure.

Referring now to FIG. 4, with the cable 150 positioned within the central channel 142, the cable 150 can be tensioned using any of various tensioners 202 (see, e.g., FIGS. 13 and 14). Tensioning the cable 150 effectively pulls the cable 150 and the arm engagement portion 154, relative to the head 102, the elongate shaft 104, and the washer 106, in the direction indicated by direction arrow 190 (see, e.g., FIGS. 4 and 12). As the cable 150 is further tensioned, the arm engagement portion 154 engages the tapered interior surfaces 120 of the arms 110 of the head 102. When the tension force applied to the cable 150 exceeds the strength of the material forming the attached ends 112 of the arms 110, engagement of the arm engagement portion 154 of the cable 150 against the tapered interior surfaces 120 of the arms 110 begins to deform the attached ends 112 of the arms 110. Deformation of the attached ends 112 of the arms 110 by the arm engagement portion 154 causes the free ends 116 of the arms 110 to deploy radially outwardly away from each other and the central axis 108 of the anchor 100 as indicated by directional arrows 192. As the tension in the cable 150 is increased, the arm engagement portion 154 of the cable 150 slides along the tapered interior surfaces 120 of the central channel 142 to increasingly deform the attached ends 112 of the arms 110 and continuously deploy, radially outwardly, the free ends 116 of the arms 110 into a deployed state. In some implementations, the deformation of the attached ends 112 is merely elastic deformation, such that upon release of the tension, the arms 110 return to an original or near-original shape. However, in other implementations, the deformation of the attached ends 112 is plastic deformation, such that upon release of the tension, the arms 110 remain in the deformed state.

In the deployed state, as shown in FIG. 4, the radial distance between the central axis 108 and the points or peaks of the teeth 132 are different such that the points or peaks of the teeth 132 are co-planar with each other along planes oblique to the central axis 108. When the head is positioned within an interior portion of a bone, deployment of the head 102 into the deployed state results in the 132 of the bone engagement features 130 of the arms 110 penetrating into the bone surrounding the head 102 (such as when the head 102 is positioned within an interior portion of the bone) or the exterior surface of the bone (such as when the head 102 is positioned exteriorly of the bone). Moreover, with the teeth 132 being oblique to the central axis 108, resistance to pull-out forces in the direction indicated by direction arrow 190 is provided via the frictional engagement between the teeth 132 and the interior portion of the bone. In this manner, deployment of the head 102 of the anchor 100 in the interior portion of the bone anchors the head 102 and thus the cable 150 within the interior portion of the bone.

The elongate shaft 104 of the anchor 100 is elongate in a lengthwise direction extending parallel to the central axis 108. The elongate shaft 104 is hollow to define the portion of the central channel 142 extending through the elongate shaft 104. In some implementations, the elongate shaft 104 has a maximum outer dimension (e.g., maximum outer diameter) that is equal to or greater than that of the head 102 of the anchor 100 when in the non-deployed state. The length of the elongate shaft 104 is based on the diametric size of the bone in which the anchor 100 is to be anchored. For example, the length of the elongate shaft 104 can be substantially equal to the distance from a first surface of the bone, in which the anchor 100 is to be anchored, to the cortex of the bone defining a second surface of the bone, opposing the first surface of the bone (e.g., on the opposite side of the bone as the first surface).

The washer 106 is coupled to an end of the elongate shaft 104 opposite that of the head 102. In this manner, the head 102 defines a driving end of the anchor 100 and the washer 106 defines a tail end of the anchor 100. Generally, the washer 106 is configured to be positioned on or exteriorly of the first surface of the bone into which the anchor 100 extends. The washer 106 includes a portion of the central axis 108 of the anchor 100, which extends through the washer 106. Accordingly, as shown in FIG. 2, the cable 150 is sized to be freely pass through the head 102, elongate shaft 104, and washer 106 via the central channel 142 of the anchor 100. In some implementations, the washer 106 has a maximum outer dimension (e.g., maximum outer diameter) that is greater than that of the elongate shaft 104. The washer 106 may include internal engagement features (e.g., hex socket) or external engagement features (e.g., hex head) that may facilitate the rotatable insertion of the anchor 100 into the bone, such as by receiving and engaging an anchor insertion tool (e.g., a wrench, screwdriver, etc.).

The anchor 100 can be manufactured or assembled in any of various ways. For example, in one implementation, at least two of the head 102, elongate shaft 104, and washer 106 are co-formed (e.g., co-molded or machined) to have a single monolithic construction. According to some implementations, the head 102, elongate shaft 104, and washer 106 are all co-formed to have a single monolithic construction. In other implementations, one or more of the head 102, elongate shaft 104, and washer 106 are separately formed and attached to each other in one or more attachment processes, such as fastening, bonding, adhering, and the like. The anchor 100 can be made from any of various materials, such as metals, metal alloys, composite materials, polymeric materials, and the like.

Referring to FIGS. 5-8, another embodiment of the anchor 100 is shown. The anchor 100 of FIGS. 5-8 is similar to the anchor 100 of FIGS. 1-4 in that the anchor 100 of FIGS. 5-8 is a bi-cortical anchor with a head 102, elongate shaft 104, and washer 106. However, the head 102 of the anchor 100 of FIGS. 5-8 is different than that of the anchor 100 of FIGS. 1-4. More specifically, instead of teeth that are non-helical, such as teeth 132 of FIGS. 1-4, the bone engagement features 130 of the head 102 of the anchor 100 of FIGS. 5-8 are teeth 134 that are helical. For example, the teeth 134 formed into the exterior surface of the arms 110 are effectively joined together to define a single helical tooth that extends circumferentially around the head 102 in helical manner. In some implementations, the teeth 134 are threads that can be threaded into a pre-formed hole in the interior portion of the bone. According to yet certain implementations, the teeth 134 are flutes that promote self-drilling of the anchor 100 into the interior portion of the bone, such that a pre-formed hole is unnecessary.

Figure 7:
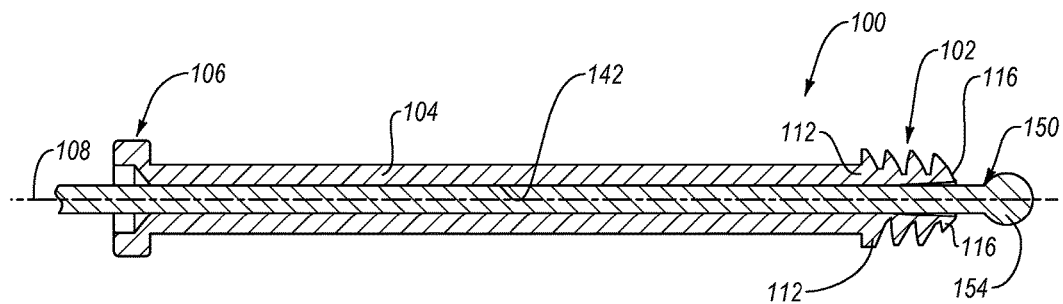
FIG. 7 is a cross-sectional side elevation view of the deployable anchor of FIG. 6, shown with a head in a non-deployed state, according to one or more embodiments of the present disclosure.

The heights of the points or peaks of the teeth 134 can be constant or vary circumferentially about the arms 110. Moreover, the teeth 134 on each arm 110 can have different heights. In this manner, in the non-deployed state, as shown in FIG. 7, the radial distance between the central axis 108 and the points or peaks of the teeth 134 can be different. For example, the heights of the teeth 134 may steadily increase in a direction extending from the free ends 116 of the arms 110 to the attached ends 112 of the arms 110. In some implementations, the elongate shaft 104 of the anchor 100 of FIGS. 5-8 has a maximum outer dimension (e.g., maximum outer diameter) that is less than that of the teeth 134 of the head 102 when in the non-deployed state.

Figure 8:
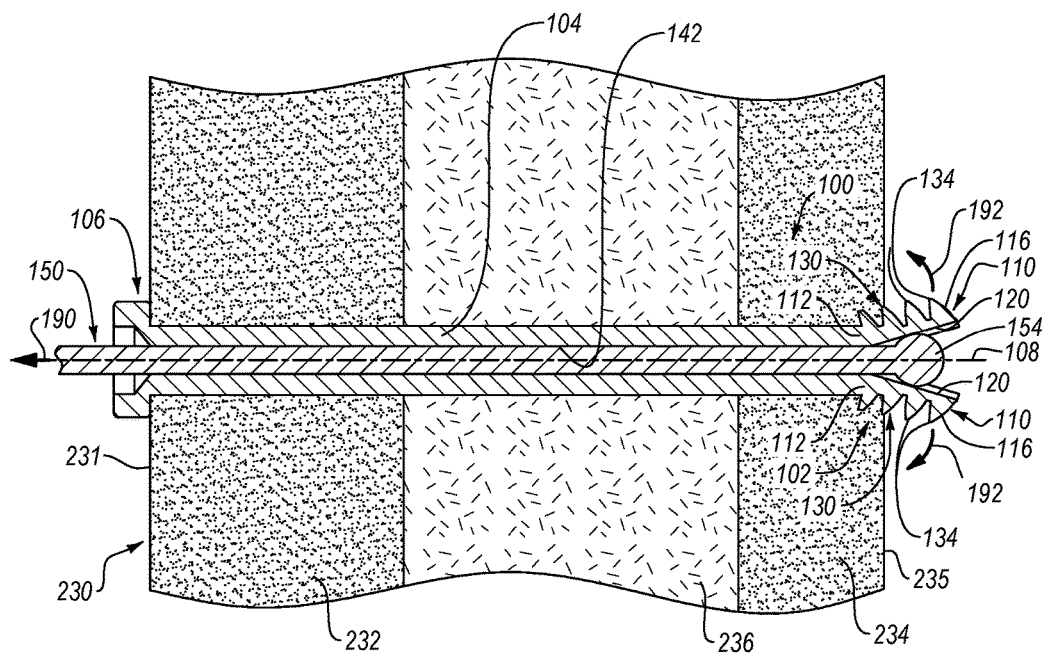
FIG. 8 is a cross-sectional side elevation view of the deployable anchor of FIG. 6, shown with the head in a deployed state, according to one or more embodiments of the present disclosure.
Figure 9:
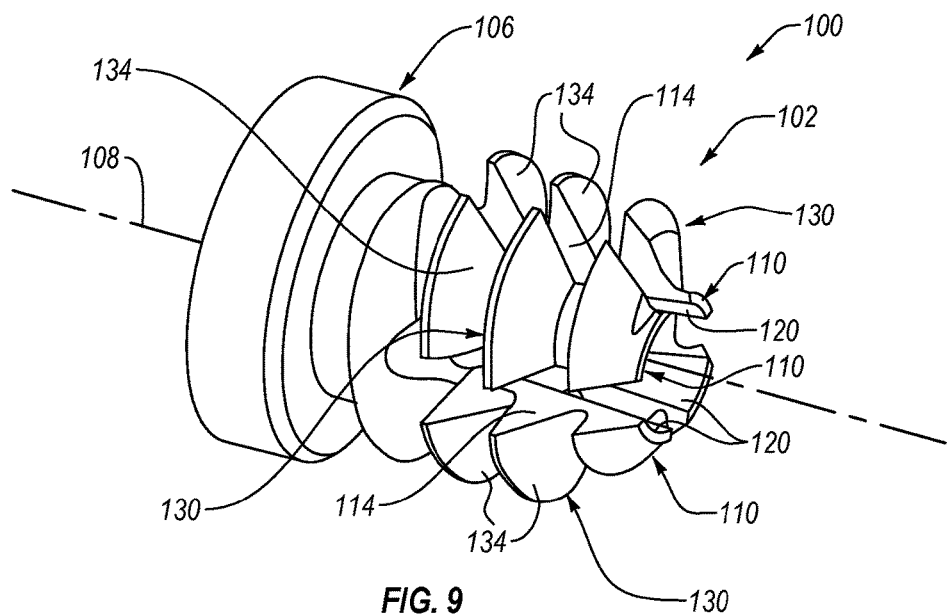
FIG. 9 is a perspective view of another deployable anchor, shown without a cable, according to one or more embodiments of the present disclosure.
Figure 10:
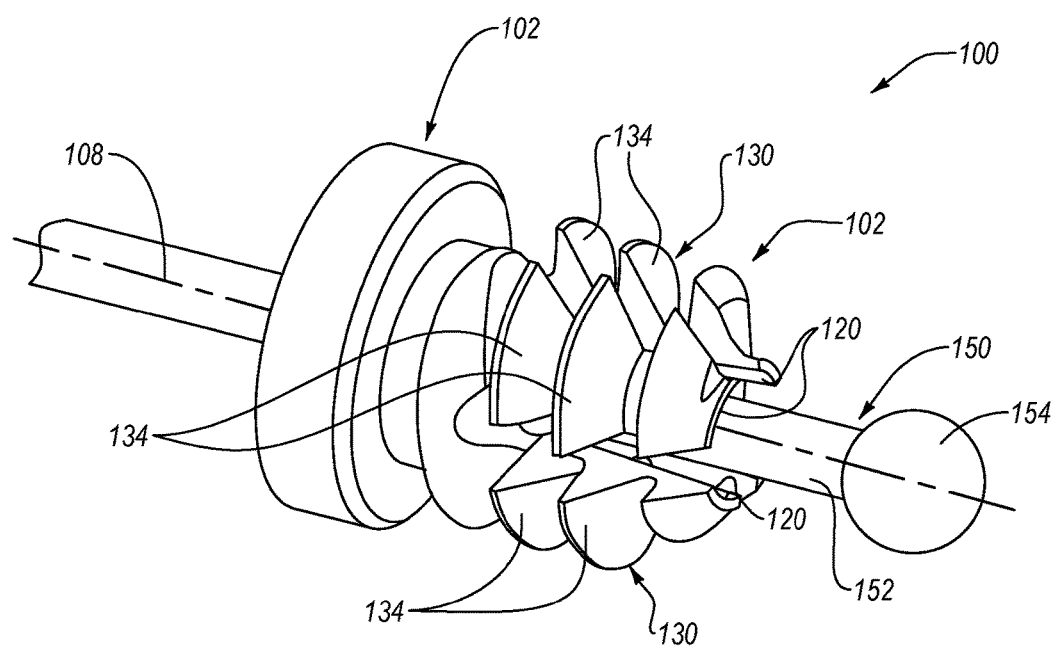
FIG. 10 is a perspective view of the deployable anchor of FIG. 9, shown with the cable, according to one or more embodiments of the present disclosure.
Figure 11:
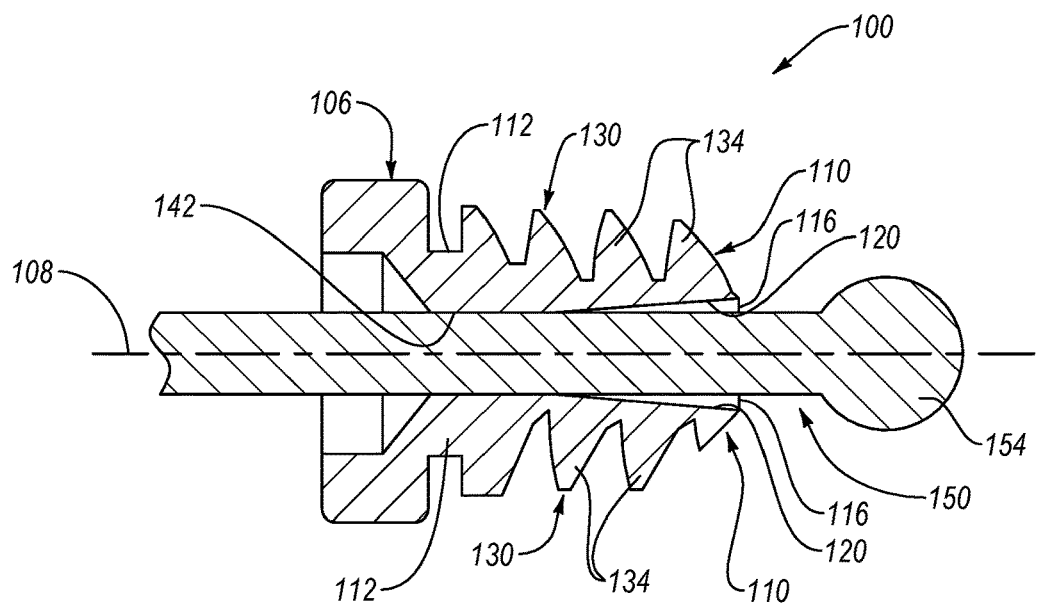
FIG. 11 is a cross-sectional side elevation view of the deployable anchor of FIG. 10, shown with a head in a non-deployed state, according to one or more embodiments of the present disclosure.

Referring to FIG. 8, with the cable 150 positioned within the central channel 142, the cable 150 can be tensioned to effectively pull the cable 150 and the arm engagement portion 154 in the direction 190. As the tension in the cable 150 is increased, the arm engagement portion 154 of the cable 150 slides along the tapered interior surfaces 120 of the central channel 142 to increasingly deform the attached ends 112 of the arms 110 and continuously deploy, radially outwardly, the free ends 116 of the arms 110 into a deployed state. In the deployed state, as shown in FIG. 8, the teeth 134 of the bone engagement features 130 of the arms 110 penetrate into the interior portion (e.g., far cortex 234) of the bone surrounding the head 102 (such as when the head 102 is positioned within an interior portion (e.g., far cortex 234) of the bone) or the exterior surface (e.g., second surface 235) of the bone (such as when the head 102 is positioned exteriorly of the bone) to resist pull-out forces in the direction indicated by direction arrow 190.

Referring to FIGS. 9-12, another embodiment of the anchor 100 is shown. The anchor 100 of FIGS. 9-12 is similar to the anchor 100 of FIGS. 5-8 in that the anchor 100 of FIGS. 9-12 includes a head 102, with teeth 134 that are helical, and a washer 106. However, unlike the anchor 100 of FIGS. 5-8, the anchor 100 of FIGS. 9-12 is a uni-cortical anchor without an elongate shaft 104. As will be explained in more detail below, because the anchor 100, shown in FIGS. 9-12, does not have an elongate shaft 104 (e.g., the washer 106 is coupled directly to the head 102 or a shaft between the washer 106 and the head 102 has a nominal length or is not elongated), the anchor 100 is defined as a uni-cortical anchor configured to extend into only a single side of the cortex of a bone.

Referring still to FIG. 12, with the cable 150 positioned within the central channel 142, the cable 150 can be tensioned to effectively pull the cable 150 and the arm engagement portion 154 in the direction 190. As the tension in the cable 150 is increased, the arm engagement portion 154 of the cable 150 slides along the tapered interior surfaces 120 of the central channel 142 to increasingly deform the attached ends 112 of the arms 110 and continuously deploy, radially outwardly, the free ends 116 of the arms 110 into a deployed state. In the deployed state, as shown in FIG. 12, the teeth 134 of the bone engagement features 130 of the arms 110 penetrate into the interior portion (e.g., near cortex 232) of the bone or an interior surface of the bone (e.g., the interior surface 237 of the near cortex 232 of the bone (see, e.g., FIG. 14)) to resist pull-out forces in the direction indicated by direction arrow 190.

Although the bone engagement features 130 of the anchor 100 of FIGS. 9-12 are shown as teeth 134 that are helical, in some embodiments, the bone engagement features 130 of the anchor 100 of FIGS. 9-12 can be teeth 132 that are non-helical (see, e.g., FIG. 2).

Figure 18:
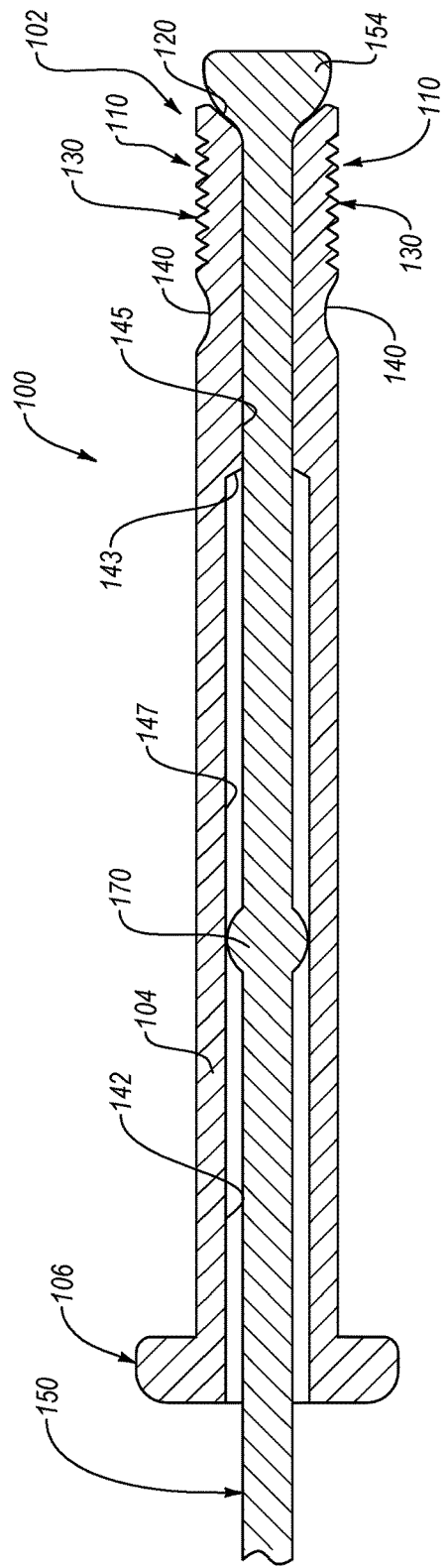
FIG. 18 is a cross-sectional side elevation view of another deployable anchor, shown with a cable, according to one or more embodiments of the present disclosure.

Referring now to FIG. 18, according to certain embodiments, the anchor 100, whether similar to the anchor 100 of FIGS. 1-4 or FIGS. 5-12, may be configured to retain the cable 150 as the anchor 100 is removed from the bone following installation of the anchor 100 in the bone. For example, after a fracture has sufficiently healed, the anchor 100 may need to be removed from the bone. Removal of the anchor 100 from the bone includes releasing the tension in the cable 150, such as by cutting the cable 150, and removing the anchor 100 out of the bone by gripping and pulling the washer 106 away from the bone. As the anchor 100 is removed from the bone, the cable 150 may have a tendency to move relative to the anchor 100 and remain in the bone. Accordingly, the cable 150 of FIG. 18 includes a plug 170, non-movably fixed to the cable and having a cross-sectional area greater than the elongate portion of the cable. In some implementations, the arm engagement portion 154 is separately attached after threading the cable with the plug through the anchor 100. With the arm engagement portion 154 engaged with the head 102, the plug 170 of the cable 150 is positioned within the central channel 142 of the elongate shaft 104 between the washer 106 and the head 102.

The central channel 142 includes a first section 147, with a cross-sectional area equal to or greater than the plug 170, and a second section 145, with a cross-sectional area less than the plug 170. The second section 145 is between the first section 147 and the head. A transition between the first section 147 and the second section 145 can be defined as a stop 143. Generally, as the anchor 100 is removed from the bone in a second direction, the untensioned cable, including the plug 170, will move within and relative to the first section 147 toward the second section 145 in a first direction, opposite the second direction, until the plug 170 contacts the stop 143, which prevents further relative movement of the plug 170 and thus the cable 150, in the first direction, toward the second section 145. In this manner, the cable 150 and the plug 170 will move in the second direction along with the anchor 100 as the anchor 100 is further removed from the bone in the second direction. As shown in FIG. 18, the arm engagement portion 154 can have a shape other than spherical, such as triangular (e.g., wedge-shaped).

Figure 19:
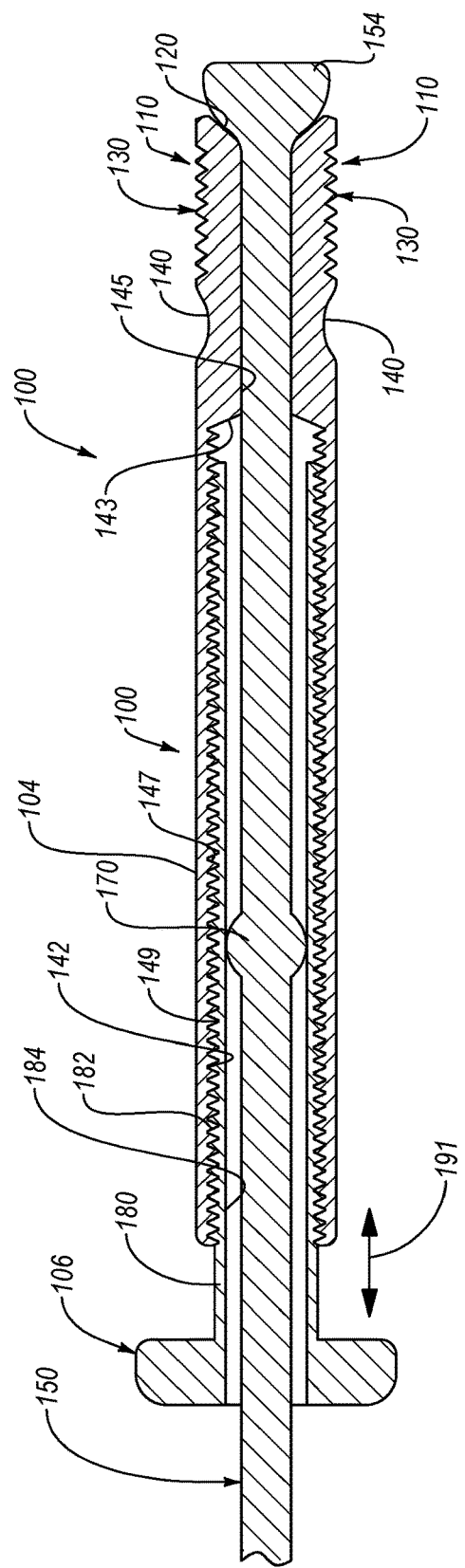
FIG. 19 is a cross-sectional side elevation view of yet another deployable anchor, shown with a cable, according to one or more embodiments of the present disclosure.

Now referring to FIG. 19, according to certain embodiments, the anchor 100, whether similar to the anchor 100 of FIGS. 1-4 or FIGS. 5-12, may be configured to promote adjustability of the length of the anchor 100 to accommodate different bone sizes and procedures. Like the anchor 100 of FIG. 18, the anchor 100 of FIG. 19 includes a central channel 142 with a first section 147, second section 145, and stop 143, and the cable 150 includes a plug 170, to facilitate co-removal of the anchor 100 and cable 150 from a bone as presented above. However, the first section 147 of the central channel 142 also includes internal threads 149, or other internal engagement features. The anchor 100 additionally includes a telescoping element 180 movably received within the first section 147 of the central channel 142. The washer 106 is fixed to an end of the telescoping element 180, which includes external threads 182, or other external engagement features, which threadably engage with the internal threads 149, or internal engagement features, of the first section 147 of the central channel 142. Rotation of the telescoping element 180 relative to the first section 147 of the central channel 142 facilitates translational movement of the telescoping element 180, as indicated by directional arrows 191, relative to the elongate shaft 104 and head 102 of the anchor 100. More specifically, relative rotation of the telescoping element 180 in a first rotational direction moves the telescoping element 180, and thus the washer 106, towards the head 102 and relative rotation of the telescoping element 180 in a second rotational direction moves the telescoping element 180, and thus the washer 106, away from the head 102. In this manner, a length of the anchor 100 (i.e., a distance between the washer 106 and the head 102) is adjustable. Accordingly, a single anchor 100 can be adjusted to any of various lengths to accommodate any of variously sized bones.

Figure 23:
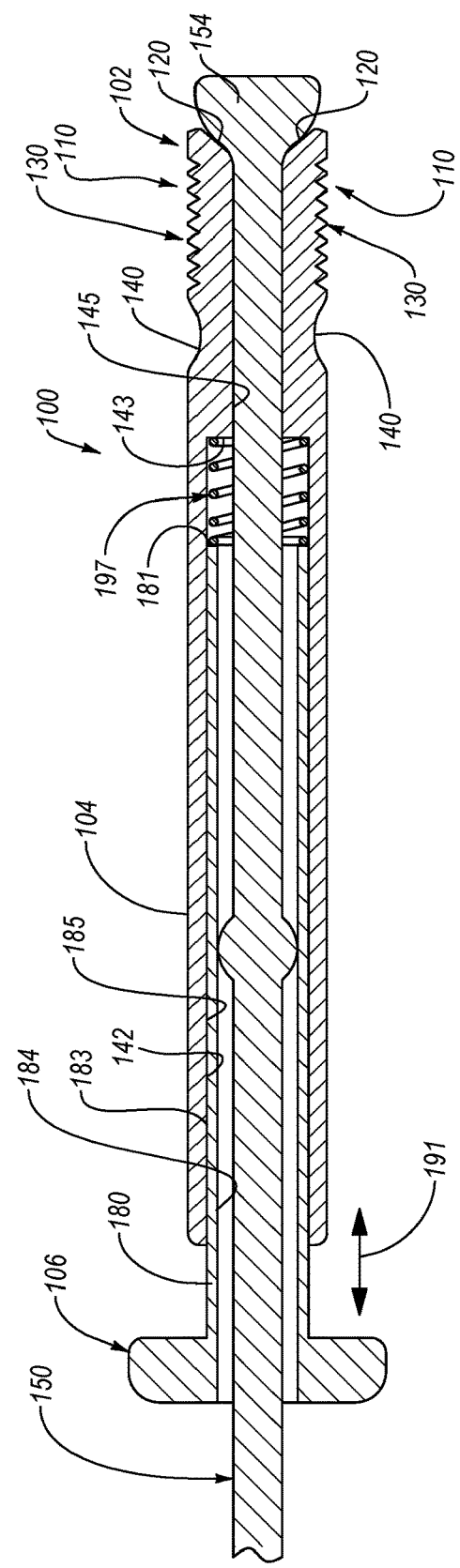
FIG. 23 is a partial cross-sectional side elevation view of another deployable anchor, shown with a head in a non-deployed state, according to one or more embodiments of the present disclosure.

As shown in FIG. 23, according to one embodiment, an anchor 100 can be configured in a manner similar to the anchor 100 of FIG. 19 to have a telescoping element 180 that is movably received within a central channel 142 for the purpose of adjusting an overall length of the anchor 100. However, instead of a threaded engagement between the telescoping element 180 and central channel 142, where adjustment of the length of the anchor 100 is provided by rotating the telescoping element 180 relative to the central channel 142, as with the anchor 100 of FIG. 19, the telescoping element 180 and central channel 142 of the anchor 100 of FIG. 23 have a slidable engagement, where adjustment of the length of the anchor 100 is provided by tensioning the cable 150 beyond a pre-calibrated force of a spring 197. The spring 197, which is not shown in cross-section, is positioned within the central channel 142 between a stop 143 and an internal end 181 of the telescoping element 180. The force necessary to fully deploy the head 102 is less than or equal to the pre-calibrated force of the spring 197.

As the cable 150 is tensioned, the head 102 is deployed and a force applied to the washer 106 toward the head 102 (discussed in more detail below) urges the telescoping element 180 along the central channel 142 toward the head 102. The external surface 183 of the telescoping element 180 and the internal surface 185 central channel 142 are smooth, which facilitates slidable engagement of the telescoping element 180 along the central channel 142. The internal end 181 of the telescoping element 180 contacts the spring 197 to apply a force to the spring 197. While the force applied to the spring 197 is less than or equal to the pre-calibrated force of the spring 197, the head can be fully deployed and the spring experiences no compression. However, once the tension in the cable 150 exceeds the pre-calibrated force of the spring 197, the spring 197 compresses, which draws the washer 106 towards the head 102 resulting in a shortening of the overall length of the anchor 100. Additional tensioning of the cable 150 further compresses the spring 197 and further shortens the anchor 100.

Figure 20:
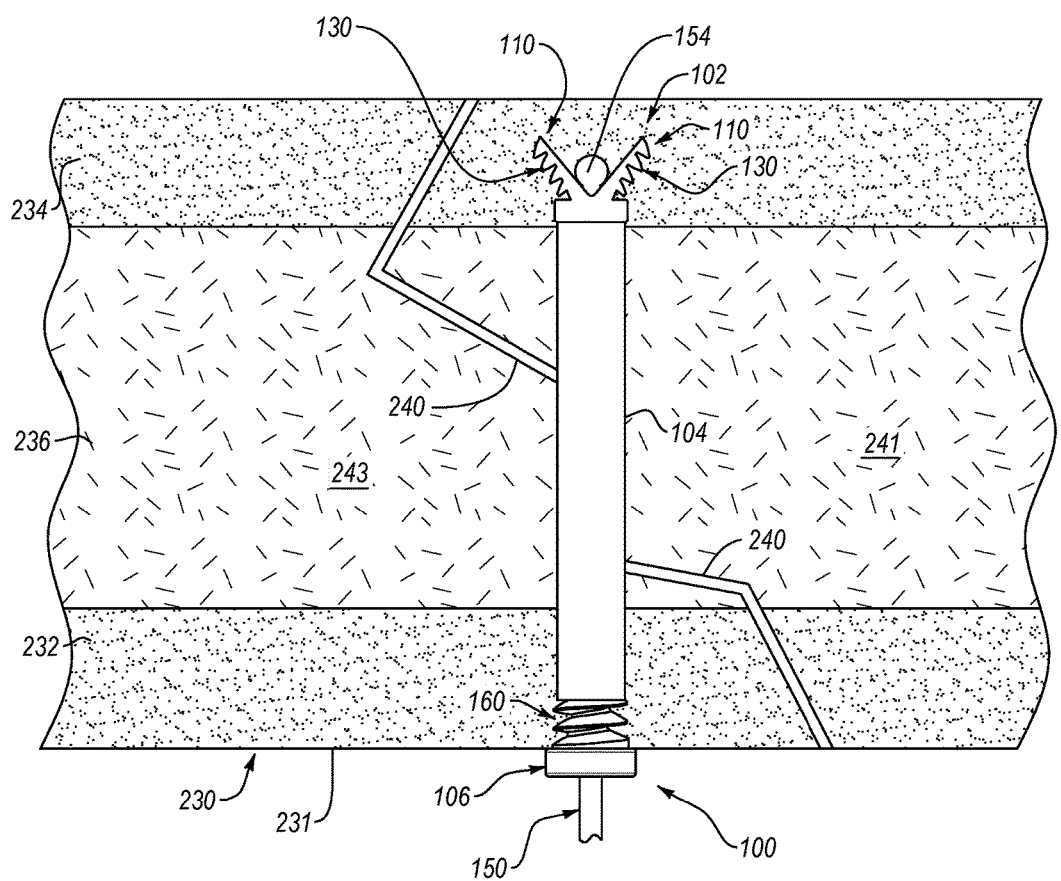
FIG. 20 is a partial cross-sectional side elevation view of an additional deployable anchor, shown with a head in a deployed state, according to one or more embodiments of the present disclosure.

Referring to FIG. 20, according to certain embodiments, the anchor 100, whether similar to the anchor 100 of FIGS. 1-4 or FIGS. 5-12, may be configured to frictionally engage both a near cortex 232 of a bone 230 and a far cortex 234 of the bone 230. Like the anchors 100 of FIGS. 1, 2, and 5-8, the anchor 100 of FIG. 20 includes a head 102, a washer 106, and an elongate shaft 104 between the washer 106 and the head 102. However, in addition to the bone engagement features 130 of the head 102, the anchor 100 of FIG. 20 also includes bone engagement features 160 proximate the washer 106. In other words, the anchor 100 includes bone engagement features 130 at the head 102 and bone engagement features 160 at the washer 106, such that the elongate shaft 104 extends between the bone engagement features 130 and the bone engagement features 160. In some implementations, the bone engagement features 160 include teeth, such as the helical teeth shown in FIG. 20. As the anchor 100 is inserted into the bone 230, such as by rotating the anchor 100 relative to the bone 230, the bone engagement features 130 may assist in the insertion process by facilitating threading of the anchor 100 into the bone. In a similar manner, when the anchor 100 has reached a sufficient depth into the bone 230 (e.g., the bone engagement features 130 have reached the far cortex 234), further insertion of the anchor 100 allows the bone engagement features 160 to thread into the near cortex 232. The additional frictional engagement provided by the bone engagement features 160 promotes additional resistance to pull-out forces on the anchor 100. Also, in some implementations, the anchor 100 of FIG. 20 can pass through a fracture 240 such that the bone engagement features 160, when frictionally engaged with the near cortex 232, help to retain together a bone segment 241, including the near cortex 232, and a bone segment 243, including the far cortex 234, where the bone segments 241, 243 are separated by the fracture 240.

Figure 21:
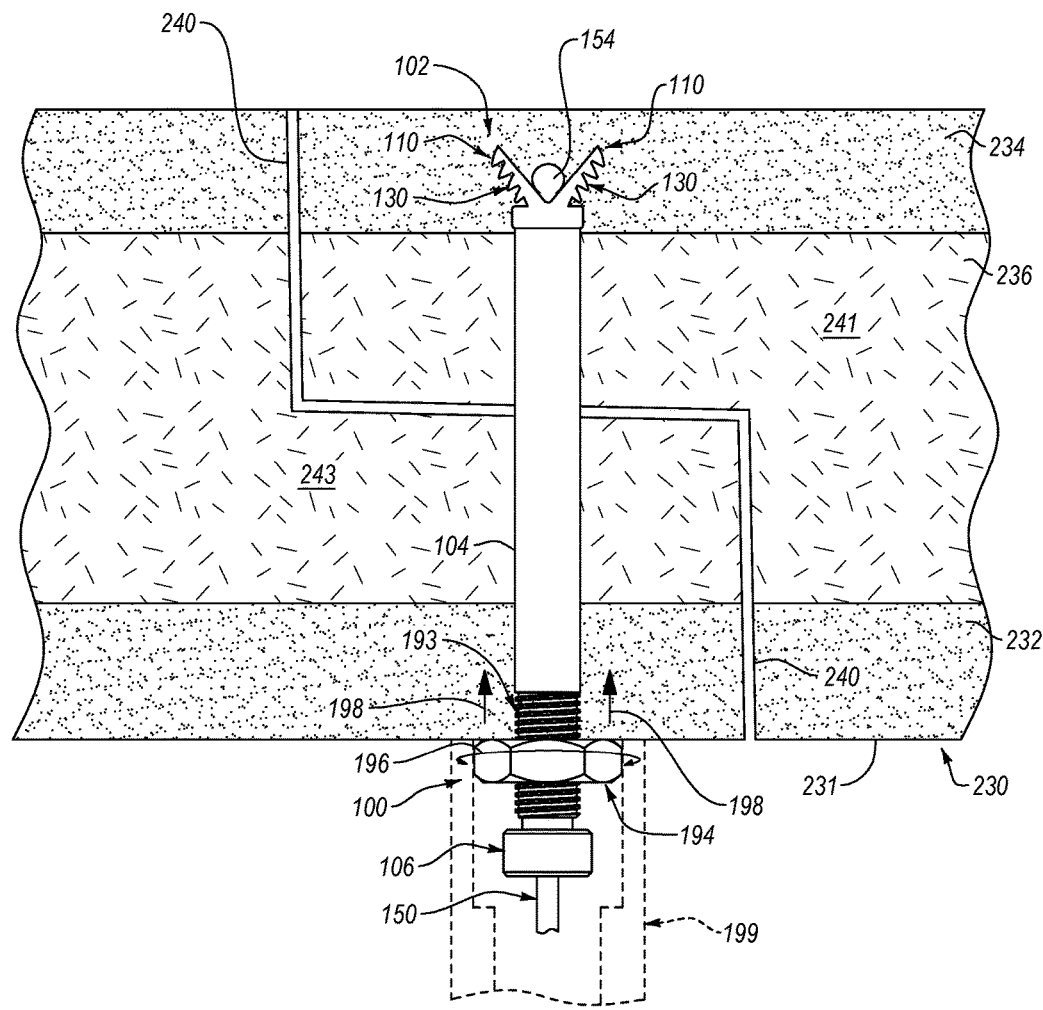
FIG. 21 is a partial cross-sectional side elevation view of another deployable anchor, shown with a head in a deployed state, according to one or more embodiments of the present disclosure.

Now referring to FIG. 21, according to certain embodiments, the anchor 100, whether similar to the anchor 100 of FIGS. 1-4 or FIGS. 5-12, may be configured to promote the compression of fractured bone segments 241, 243 through which the anchor 100 is inserted. Like the anchors 100 of FIGS. 1, 2, and 5-8, the anchor 100 of FIG. 20 includes a head 102, a washer 106, and an elongate shaft 104 between the washer 106 and the head 102. However, the anchor 100 of FIG. 21 further includes external threads 193, or other external engagement features, between the washer 106 and the elongate shaft 104. Additionally, the anchor 100 of FIG. 21 includes a compression nut 194 with internal threads (not shown) threadably engaged with the external threads 193. Threaded engagement between the compression nut 194 and the external threads 193 facilitates the translational movement toward the head 102, as indicated by directional arrows 198, as the compression nut 194 is rotated in one rotational direction and away from the head 102 as the compression nut 194 is rotated in an opposite rotational direction. Accordingly, after the anchor 100 is anchored to the bone 230 (e.g., the head 102 is deployed to frictionally engage the bone via tensioning of the cable 150), the compression nut 194 is rotated to translationally move the compression nut 194 toward the head 102 and into contact with a first surface 231, which is an external surface, of the near cortex 232 to compress together the bone segments 241, 243, separated by the fracture, and promote healing of the bone 230.

The compressive force on the bone segments 241, 243 is adjustable by rotating the compression nut 194. In one implementation, the compression nut 194 is rotatable by a tool 199, such as a socket wrench, that rotatably engages the compression nut 194, such as a polygonal outer periphery of the compression nut 194. The tool 199 can be at least partially hollow to allow passage of the washer 106 and cable 150 through the tool 199 while the tool 199 is engaged with the compression nut 194.

Figure 22:
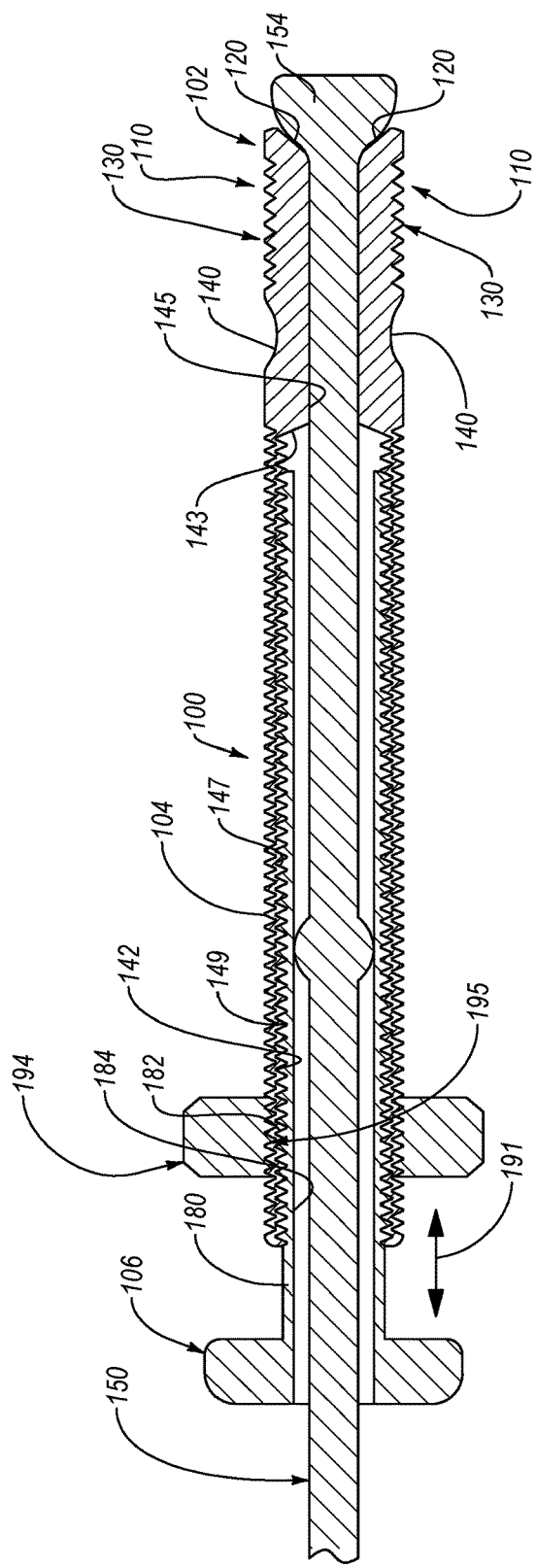
FIG. 22 is a cross-sectional side elevation view of yet another deployable anchor, shown with a head in a non-deployed state, according to one or more embodiments of the present disclosure.

Referring to FIG. 22, in one embodiment, an anchor 100, whether similar to the anchor 100 of FIGS. 1-4 or FIGS. 5-12, may be configured to promote both the compression of fractured bone segments 241, 243, as with the anchor 100 of FIG. 21, and adjustability of the length of the anchor 100 to accommodate different bone sizes and procedures, as with the anchor 100 of FIG. 19. More specifically, the first section 147 of the central channel 142 of the anchor 100 of FIG. 22 includes internal threads 149, or other internal engagement features, and the anchor 100 includes the telescoping element 180, which includes the external threads 182, or other external engagement features, which threadably engage with the internal threads 149, or internal engagement features, of the first section 147 of the central channel 142. Such a configuration facilitates relative rotation of the telescoping element 180 for adjustment of the length of the anchor 100. Additionally, the anchor 100 of FIG. 22 further includes external threads 193, or other external engagement features, and a compression nut 194 with internal threads 195 threadably engaged with the external threads 193. Such a configuration allows the compression nut 194 to move into contact with an external surface of a bone to compress together bone segments of the bone 230.

Figure 24:
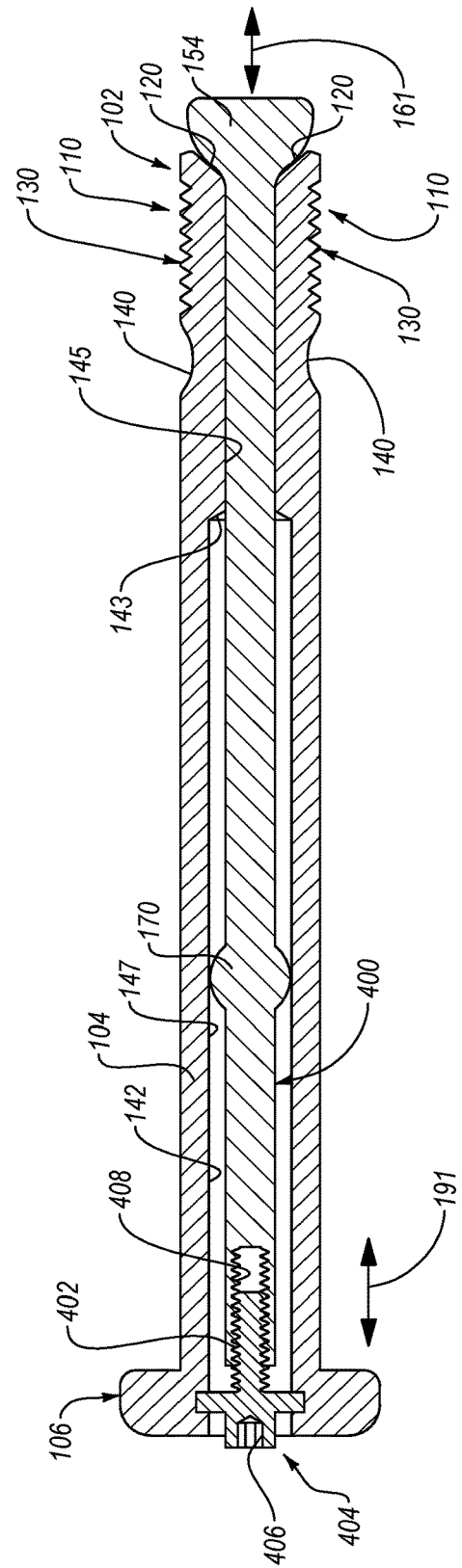
FIG. 24 is a cross-sectional side elevation view of yet another deployable anchor, shown with a head in a non-deployed state, according to one or more embodiments of the present disclosure.

Now referring to FIG. 24, according to another embodiment, an anchor 100, like other anchors described herein, includes a head 102, an elongate shaft 104, and a washer 106. However, instead of tensioning a cable 150, which is flexible as defined herein, to deploy the head 102, the anchor 100 of FIG. 24 utilizes a rod 400, which is more rigid than the cable 150, to deploy the head 102. The rod 400 is positioned within the central channel 142 and can include a plug 170. Additionally, the rod 400 includes internal threads 408 formed in a tail end of the rod 400. The anchor 100 further includes a driver 404 rotatably coupled with the elongate shaft 104 and/or the washer 106 (such as via an interior annular slot formed in the central channel 142). The driver 404 includes external threads 402 threadably engaged with the internal threads 408 of the rod 400. Due to the threadable engagement between the external threads 402 of the driver 404 and the internal threads 408 of the rod 400, rotation of the driver 404 relative to the rod 400 translationally moves an arm engagement portion 154, at a head of the rod 400, toward the washer 106. As the arm engagement portion 154 moves in this manner, engagement with the head 102 causes the arms 110 to deploy. To facilitate rotation of the driver 404, the driver 404 can include a recess 406 configured to receive a tool (e.g., drill, screwdriver, wrench, etc.) that is appropriate for rotatably driving the driver 404. In some implementations, the recess 406 has a hexagonally-shaped cross-section for receiving a hexagonally-shaped tool. Although, in the illustrated embodiment, the rod 400 has internal threads 408 and the driver 404 has external threads 402, in other embodiments, the rod 400 can have external threads and the driver 404 can have internal threads. In yet some embodiments, other techniques and mechanical arrangements can be used to facilitate translational movement of the rod 400 along the central channel 142.

Although the embodiments of the anchor 100 of FIGS. 1-23 are shown with and described to have a cable 150, which is tensioned to deploy the head 102, in other embodiments, the anchor 100 of FIGS. 1-23 may utilize another actuator, instead of the cable, such as a shaft or rod, that can be moved (e.g., pulled, slid, rotated, etc.) relative to the head 102 to deploy the head 102. However, embodiments of the anchor 100 with an actuator other than a cable may not provide the benefits of the anchor 100 with an actuator that is a cable, such as being able to tension the actuator to a measurable tension.

As shown in FIGS. 13-16, according to some embodiments, a system 200 for stabilizing a bone 230 is shown. The system 200 includes a fixation device 204. Generally, the fixation device 204 is any of various devices coupled with the bone, positioned externally of the bone 230, and configured to facilitate fixation or stabilization of the bone 230. The fixation device 204 can be an internal fixation device located on a surface of the bone 230 beneath the skin (see, e.g., FIGS. 13 and 14) or an external fixation device located externally of the skin (see, e.g., FIGS. 15 and 16).

In the illustrated embodiment of FIGS. 13 and 14, the fixation device 204 is an internal fixation device in the form of a plate 205 that is positioned on or abuts a first surface 231 of the bone 230. Moreover, the plate 205 is positioned to span a fracture 240 in the bone 230. Although not necessary, the plate 205 can include one or more recesses 210 each configured to receive a fastener or anchor for securing the plate 205 to the bone 230. The plate 205 can have any of various lengths and any number of recesses 210 depending on the medical procedure (e.g., the type or severity of the fracture 240) and size of the bone 230.

In one implementation, although not necessary, the system 200 includes at least one fastener. The fastener can be a bi-cortical fastener 206 or a uni-cortical fastener 208. The bi-cortical fastener 206 is sized to extend from engagement with a recess 210 of the plate 205, through a near cortex 232 of the bone 230 (i.e., the portion of the cortex of the bone 230 defining the surface of the bone 230 through which an anchor 100 enters the bone 230 (e.g., the first surface 231)) and a medullary cavity 236 of the bone 230, to a far cortex 234 of the bone 230 (i.e., the portion of the cortex of the bone 230 defining the surface of the bone 230 opposite the surface through which an anchor 100 enters the bone 230 (e.g., the second surface 235 opposite the first surface 231). In contrast, the uni-cortical fastener 208 is sized to extend from engagement with a recess 210 of the plate 205 through only the near cortex 232 and the medullary cavity 236 of the bone 230. In other words, the uni-cortical fastener 208 extends into only one portion of the cortex of the bone 230. Although the system 200 illustrated in FIGS. 13 and 14 includes two fasteners, one bi-cortical fastener 206 and one uni-cortical fastener 208, in other embodiments, the system 200 can include fewer or more than two fasteners and/or all bi-cortical fasteners 206, all uni-cortical fasteners 208, or any combination of bi-cortical and uni-cortical fasteners. Generally, in some embodiments, the system 200 includes at least one fastener on each side of the fracture 240.

The system 200 of FIG. 13 further includes three anchors 100, which are bi-cortical anchors, each with a washer 106 engaged with a respective one of three recesses 210 formed in the plate 205. In some implementations, each recess 210 of the plate 205 may have a curved surface for engaging the washer 106. Accordingly, as shown in FIG. 6, in such implementations, the washer 106 may have a curved undersurface 107 that complements the curved surface of the recess 210 for facilitating a complementary or nested engagement with the recess 210. The complementary curved surfaces promote secure engagement between the washer 106 and the recess 210 while accommodating different angular orientations of the anchor 100 relative to the plate 205. Alternatively, instead of a curved undersurface 107 that facilitates nested engaged with the recess 210 of the plate 205, in some embodiments, the washer 106 may have threads (e.g., external threads) that engage corresponding threads (e.g., internal threads) formed in the recess 210 to facilitate threaded engagement between the washer 106 and the recess 210 of the plate 205.

At least two of the anchors 100 are positioned on opposite sides of the fracture 240. The anchors 100 of the system 200 in FIG. 13 extend from engagement with a recess 210 of the plate 205, through the near cortex 232 and the medullary cavity 236 of the bone 230, to at least the far cortex 234 of the bone 230. Referring to the anchor 100 on the left-hand side of the fracture 240, as viewed in FIG. 13, the head 102 of the anchor 100, with the head 102 in the non-deployed state and the cable 150, not yet tensioned, passing through the head 102, is inserted into the bone 230 from the near cortex 232, through the medullary cavity 236, to the far cortex 234 such that the head 102 is positioned within the far cortex 234. In contrast, the head 102 of the anchor 100 on the far right-hand side of the fracture 240, as viewed in FIG. 13, is inserted into the bone 230 from the near cortex 232, through the medullary cavity 236 and far cortex 234, to beyond or outside of the far cortex 234.

In one implementation, the bone engagement features 130 include teeth 132, which are non-helical, and the head 102 is inserted into the bone 230 through a pilot hole pre-formed in the bone 230, such as with a drill bit, and sized to be diametrically equal to or larger than that of the teeth 132. In some implementations, the pilot hole can be smaller than that of the teeth 132.

According to other implementations, as shown, the bone engagement features 130 include the teeth 134, which are helical, and the head 102 is inserted into the bone 230 by screwing (e.g., rotating) the head 102 into the bone 230. In one implementation, the head 102, with the teeth 134, is screwed into the bone 230 through a pilot hole pre-formed in the bone 230. According to yet another implementation, the head 102, with the teeth 134, is self-drilled into the bone 230.

After the head 102 is inserted through the near cortex 232 and partially or entirely through the far cortex 234 of the bone 230 and positioned, in the non-deployed state, in or external to the far cortex 234 of the bone 230, the tensioner 202 can be used to tension the cable 150 to a desirable tension and cause the head 102 to deploy into the deployed state, as represented by the anchors 100 on the right-hand side of the fracture 240, as viewed in FIG. 13. Deployment of the head 102, of the anchor 100 with the head 102 in the far cortex 234, causes the bone engagement features 130 to frictionally engage the interior of the far cortex 234, which anchors the anchor 100 to the bone 230. In contrast, deployment of the head 102, of the anchor 100 with the head 102 external to, or extending entirely through the far cortex 234 of the bone 230, causes the bone engagement features 130 to frictionally engage the second surface 235 (e.g., external surface) of the bone 230, which anchors the anchor 100 to the bone 230. In this manner, the anchor 100 can extend through the bone from one side of the bone and frictionally engage an outer surface of an opposite side of the bone while approaching the bone from only one side of the bone (e.g., requiring only one incision). As defined herein, a head 102 of an anchor 100 extends entirely through the far cortex 234 when at least a portion of the head 102 penetrates through or protrudes from the second surface 235 of the bone 230. With the tension in the cable 150 at the desirable tension, a crimp 203 can be non-movably affixed to the cable 150 at the washer 106. The crimp 203 maintains the cable 150 in tension by engaging the washer 106 and acting as a stop to prevent the cable from retracting back through the washer 106.

The system 200 of FIG. 14 is similar to the system 200 of FIG. 13, except instead of anchors 100 that are bi-cortical, the system 200 of FIG. 14 includes three anchors 100 that are uni-cortical each with a washer 106 engaged with a respective one of three recesses 210 formed in the plate 205 and positioned on opposite sides of the fracture 240. The anchors 100 of FIG. 14 extend from engagement with a recess 210 of the plate 205, at least partially through only the near cortex 232 of the bone 230. In other words, the anchors 100 of the system 200 of FIG. 14 enter the bone 230 at the near cortex 232 and terminate in the near cortex 232, or beyond the near cortex 232, without entering the far cortex 234. The anchors 100 of the system 200 of FIG. 14 can be inserted into the bone 230 and the cables 150 of the anchors 100 can be tensioned, to deploy the heads 102 of the anchors 100, in the same manner as described above for the anchors 100 of FIG. 13. For the anchors 100 with heads 102 within the near cortex 232, deployment of the head 102 causes the bone engagement features 130 to frictionally engage the interior of the near cortex 232, which anchors the anchors 100 to the bone 230. In contrast, for the anchor 100 with the head 102 external to, or extending entirely through, the near cortex 232 of the bone 230 without entering the far cortex 234, (e.g., the anchor 100 on the far right-side of the fracture 240 as viewed in FIG. 14), deployment of the head 102 (e.g., within the medullary cavity 236) causes the bone engagement features 130 to frictionally engage an interior surface 237 of the near cortex 232 of the bone 230, which anchors the anchor 100 to the bone 230. The interior surface 237 of the near cortex 232 abuts the medullary cavity 236 of the bone 230.

In one embodiment, for example, the system 200 of FIG. 14, with uni-cortical anchors, includes only uni-cortical fasteners 208. Accordingly, the medullary cavity 236 is not obstructed with fasteners or anchors. With the medullary cavity 236 being unobstructed, an intra-bone fixation device, such as an intramedullary rod, can be inserted into and through the medullary cavity 236 while the plate 205 is mounted on the bone 230.

Although the system 200 of FIG. 13 includes three anchors 100 that are bi-cortical and the system 200 of FIG. 14 includes three anchors 100 that are uni-cortical, the system 200 can include fewer or more than three anchors and/or the anchors 100 of the system 200 can include both bi-cortical anchors and uni-cortical anchors.

In some embodiments, it may be desirable to control the amount of flex, stiffness, or movement of the plate 205 relative to the bone 230 (and thereby the relative movement of the bone fragments relative to one another) depending on the type of fracture 240 and/or a desired method of treating the fracture 240. For example, for some types of fractures 240 or treatments, some relative movement of the fractured portions of a bone can be beneficial for healing the fracture 240. For such fractures and treatments, a relatively loose fit between the plate 205 and the bone 230 is desired. Alternatively, for other types of fractures 240 or treatments, relative non-movement between fractured portions of a bone may be more beneficial for healing the fracture 240. For these fractures and treatments, a relatively tight fit between the plate 205 and the bone 230 is desired. A desired relative tightness or looseness of the fit between the plate 205 and the bone 230 can be achieved by controlling the tension in the cables 150 of the anchors 100 with the tensioner 202. For example, the higher the tension in the cables 150 of the anchors 100, the tighter the fit between the plate 205 and the bone 230, and vice versa.

Figure 15:
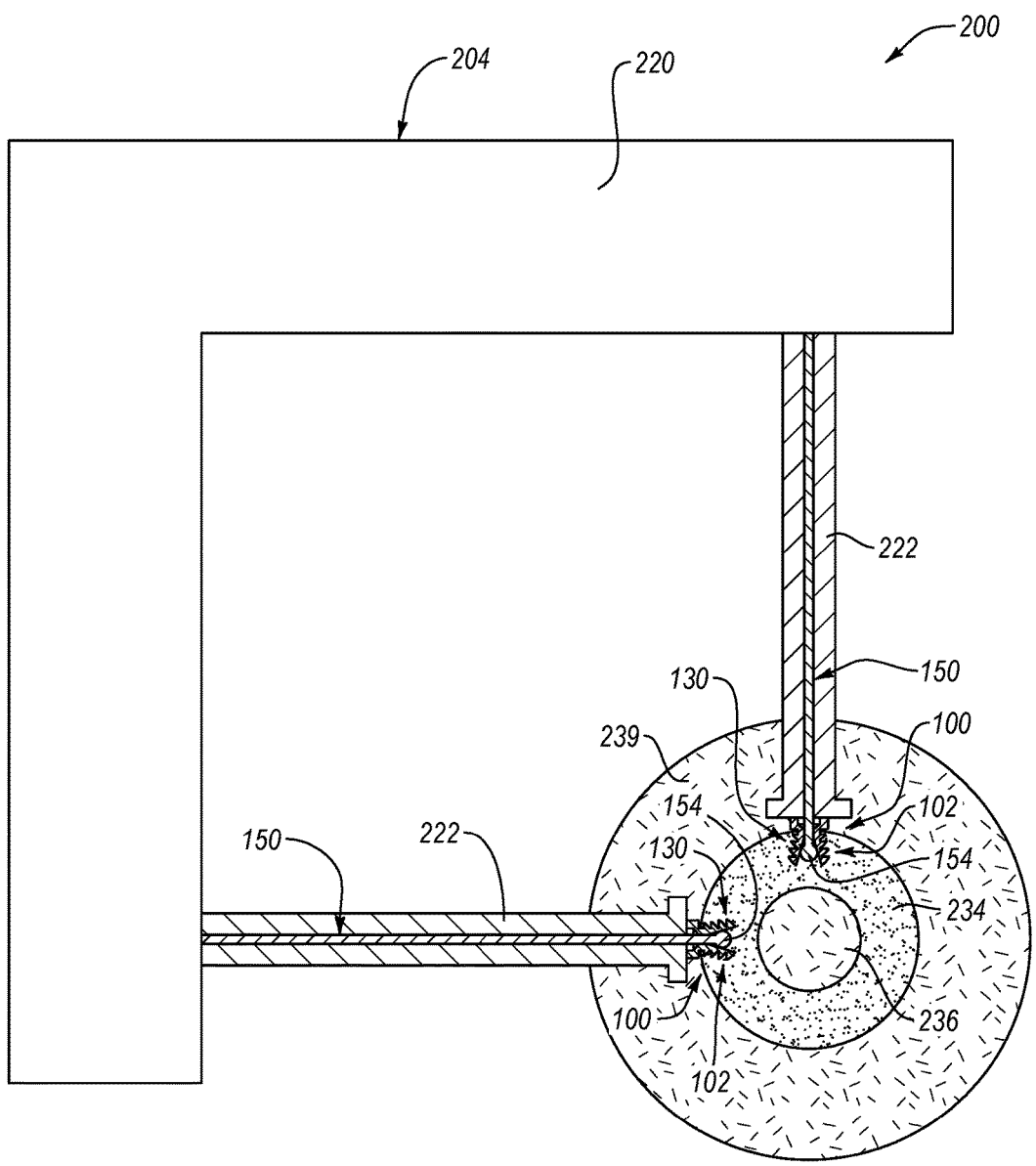
FIG. 15 is a cross-sectional end view of yet another system for stabilizing a bone, according to one or more embodiments of the present disclosure.
Figure 16:
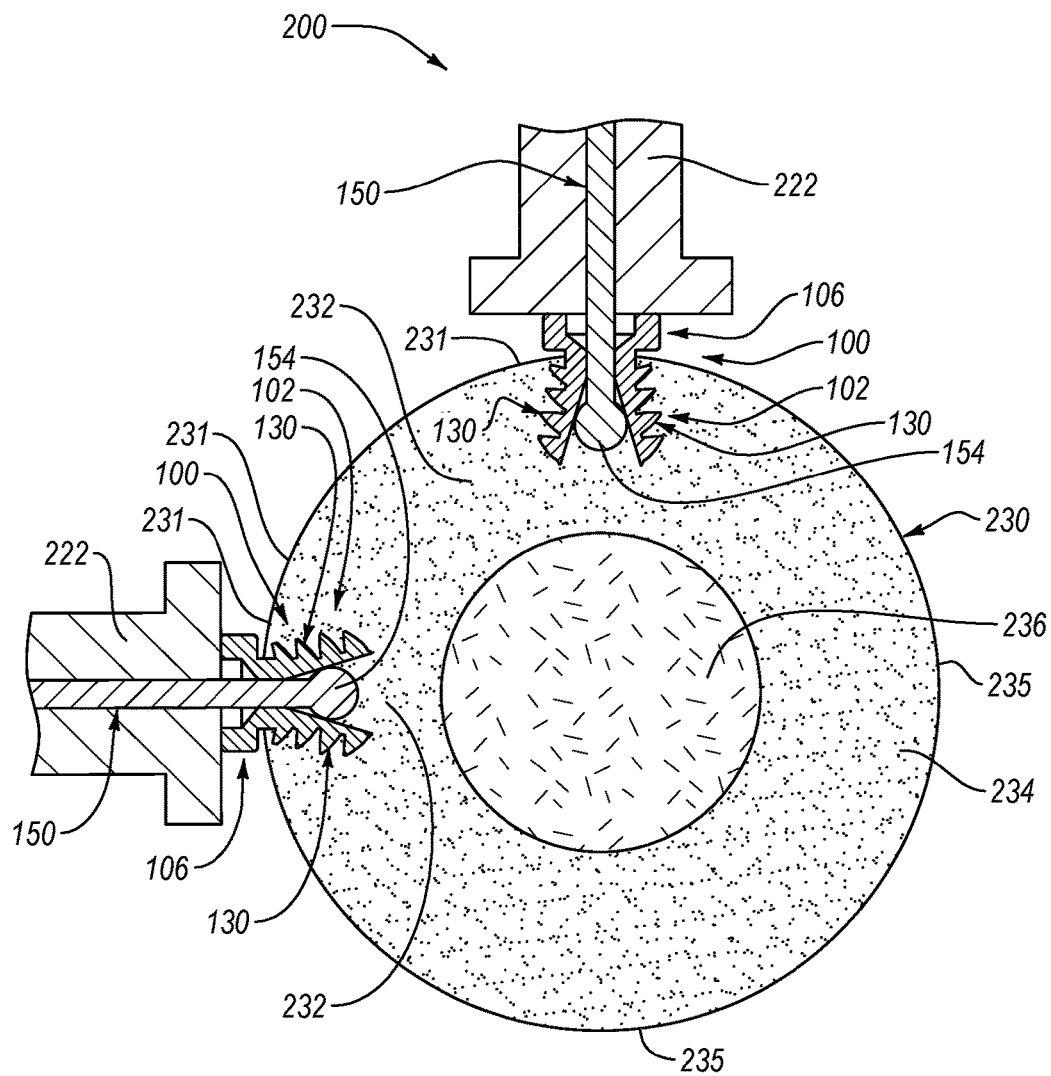
FIG. 16 is a cross-sectional end view of a portion of the system of FIG. 15, according to one or more embodiments of the present disclosure.

As shown in FIGS. 15 and 16, according to another embodiment, a system 200 for stabilizing a bone 230 is shown. Like the system 200 of FIGS. 13 and 14, the system 200 of FIGS. 15 and 16 includes a fixation device 204 mounted to the bone 230 via anchors 100. However, instead of an internal fixation device, such as plate 205, mounted on the bone 230, in the system 200 of FIGS. 15 and 16, the fixation device 204 is an external fixation device, such as a stand-off external fixator 220. The stand-off external fixator 220 can be, or include, any of various external fixators, such as bone fixation rails, bars, plates, rings, members, arcs, arches, and the like, that is coupled to, but positioned externally of the skin and other tissue 239 surrounding the bone 230 via one or more stand-off rods 222. Each stand-off rod 222 is hollow so as to define a central channel through which the cable 150 may pass.

The system 200 of FIGS. 15 and 16 further includes two anchors 100, which are uni-cortical anchors, each with a washer 106. The heads 102 of the anchors 100 are embedded or anchored in or to the near cortex 232 of the bone 230. Accordingly, the medullary cavity 236 of the bone 230 is unobstructed by the anchors 100. As mentioned above, with the medullary cavity 236 being unobstructed, an internal fixation device, such as an intramedullary rod, can be inserted into and through the medullary cavity 236 while the stand-off external fixator 220 is mounted to the bone 230. Although the bone engagement features 130 of the anchors 100 of the system 200 of FIGS. 15 and 16 are shown as including helical teeth, the bone engagement features 130 can include non-helical teeth or other types of bone engagement features.

The anchors 100 of the system 200 of FIGS. 15 and 16 are shown in the deployed state due to the cables 150 being tensioned to a desirable tension. Although not shown, the system 200 can include a tensioner for tensioning the cables 150 to the desirable tension. Prior to tensioning the cables 150, the cables 150 are passed through a respective one of the stand-off rods 222, which are coupled to (e.g., mounted on) a washer 106 of a respective one of the anchors 100. In one implementation, the stand-off rods 222 are coupled to the washers 106 such that the stand-off rods 222 extend from the bone 230 transversely away from a central axis of the bone 230. However, in other implementations, the stand-off rods 222 extend from the bone 230 obliquely relative to the central axis of the bone 230. The stand-off external fixator 220 is configured such that for each anchor and stand-off rod 222 and with the cable 150 passing through the stand-off rod 222, tensioning of the cable 150 not only deploys the head 102 of the anchor 100, but also fixedly secures the stand-off external fixator 220 to the washer 106 of the anchor 100 by effectively clamping the stand-off rod 222 down on the washer 106. In some implementations, with the tension in the cable 150 at the desirable tension, a crimp can be non-movably affixed to the cable 150 at the stand-off external fixator 220 to maintain the cable 150 in tension and keep the stand-off external fixator 220 fixedly secured to the anchor 100.

Figure 17:
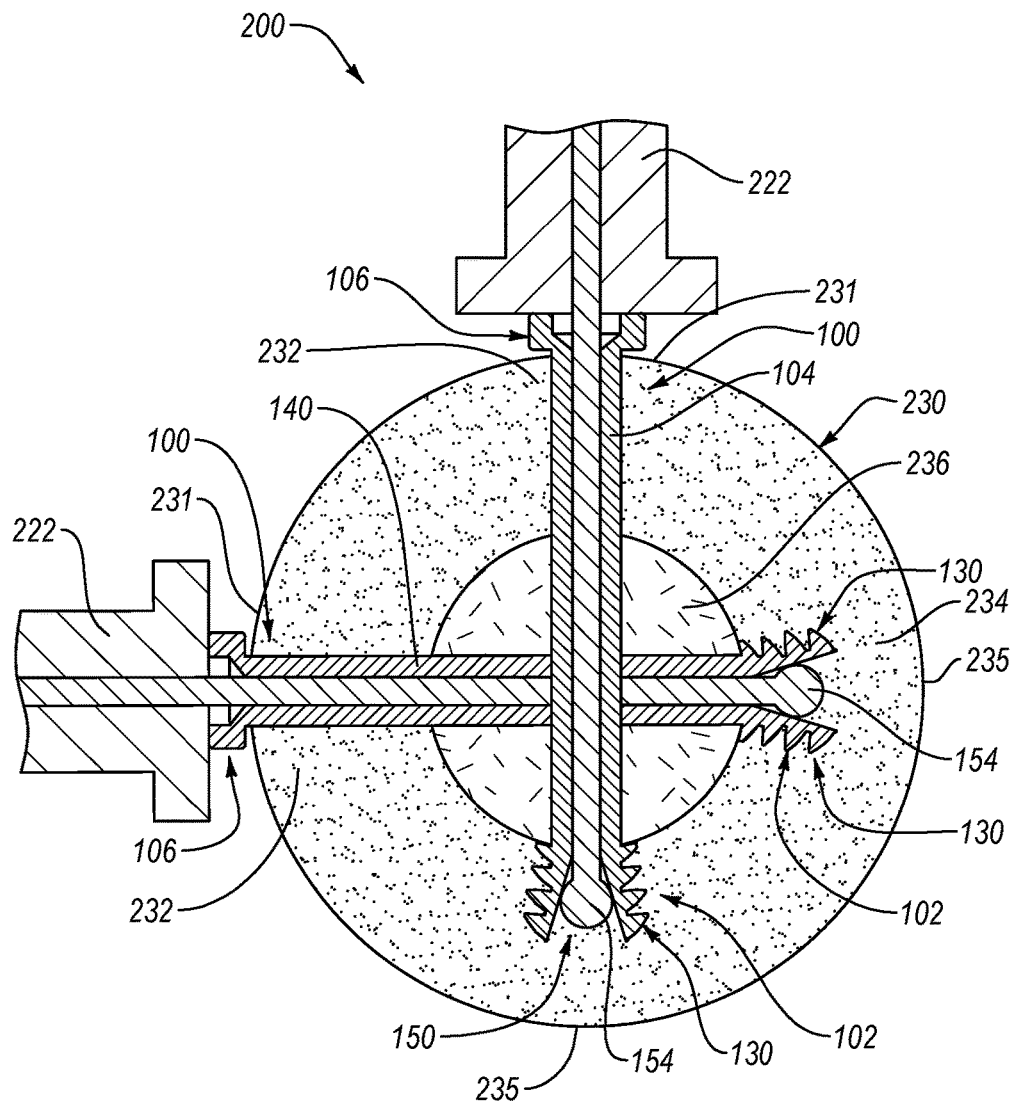
FIG. 17 is a cross-sectional end view of a portion of another system for stabilizing a bone, according to one or more embodiments of the present disclosure.

As shown in FIG. 17, according to another embodiment, a portion of a system 200 for stabilizing a bone 230 is shown. Like the system 200 of FIGS. 15 and 16, although not shown, the system 200 of FIG. 17 includes a stand-off external fixator 220 with one or more stand-off rods 222. Additionally, like the system 200 of FIGS. 15 and 16, the system 200 of FIG. 17 further includes two anchors 100 each with a washer 106. However, instead of uni-cortical anchors, the anchors 100 of the system 200 of FIG. 17 are bi-cortical anchors with heads 102 embedded or anchored in or on the far cortex 234 of the bone 230. Accordingly, the medullary cavity 236 of the bone 230 is partially obstructed by the anchors 100 in the system 200 of FIG. 17. Although the bone engagement features 130 of the anchors 100 of the system 200 of FIG. 17 are shown as including helical teeth, the bone engagement features 130 can include non-helical teeth or other types of bone engagement features. In some implementations, the bi-cortical nature of the anchors 100 of the system 200 of FIG. 17 may help facilitate strength and stability of the coupling between the stand-off external fixator 220 and the bone 230.

Figure 25:
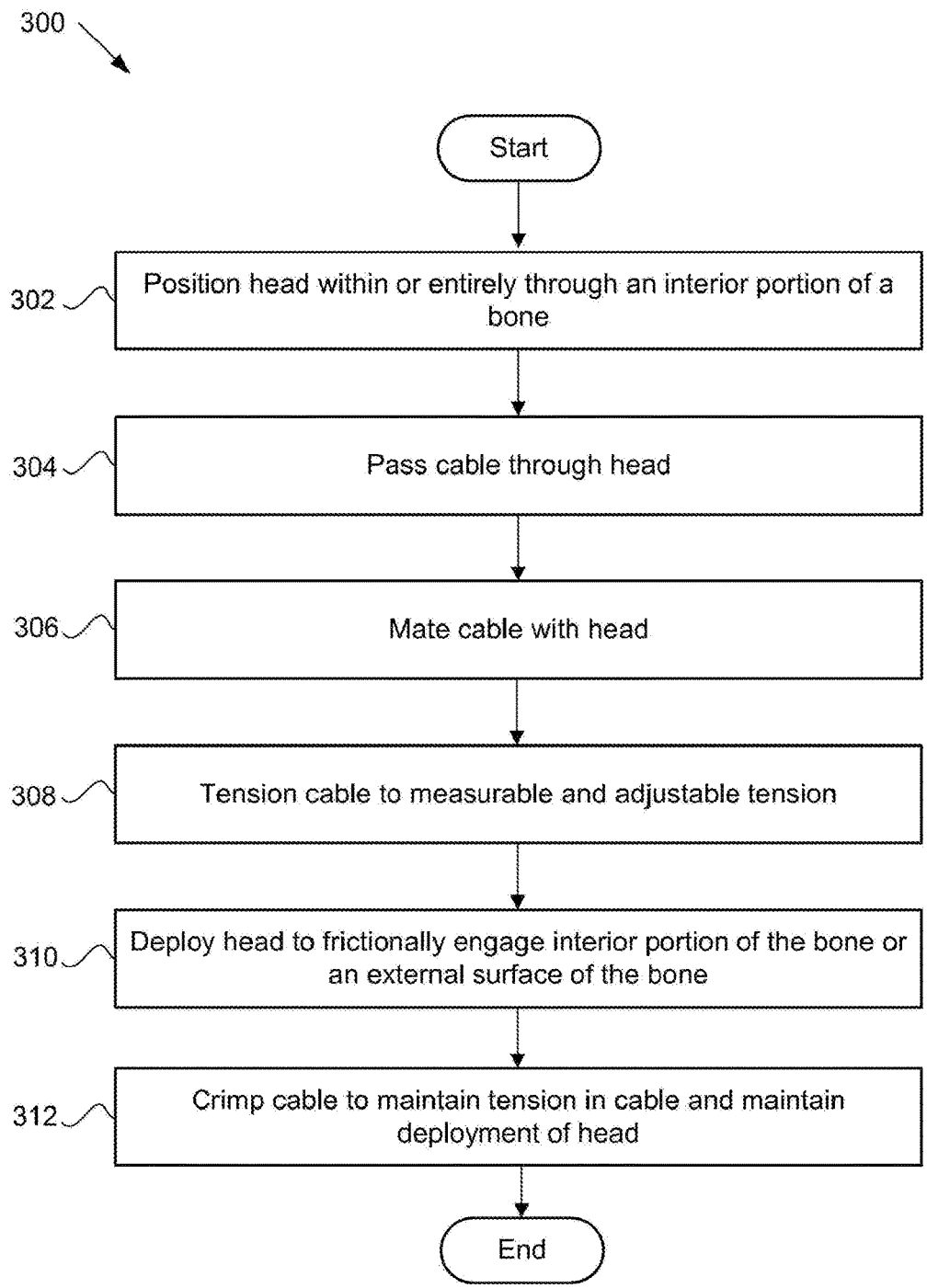
FIG. 25 is a schematic flow diagram of a method of anchoring cable to bone, according to one or more embodiments of the present disclosure.

Now referring to FIG. 25, according to one embodiment, a method 300 of anchoring cable to bone includes positioning a head within or entirely through an interior portion of a bone at 302. The interior portion of the bone can be a near cortex or a far cortex of the bone, as defined herein, depending on whether the anchor, of which the head forms a part, is a uni-cortical anchor or a bi-cortical anchor. In some implementations, positioning the head within or entirely through the interior portion of the bone at 302 may include pre-forming a hole in the bone through which the anchor is inserted into the bone. Alternatively, in certain implementations, positioning the head within the interior portion of the bone at 302 may include screwing the head into the bone or drilling a hole into the bone with the head.

Additionally, the method 300 includes passing a cable through the head at 304. In some implementations, passing the cable through the head at 304 is executed prior to positioning the head within or entirely through the interior portion of the bone at 302. More specifically, the head and cable can be collectively positioned within or entirely through the interior portion of the bone. However, in some embodiments, passing the cable through the head at 304 is executed after positioning the head within or entirely through the interior portion of the bone at 302. The method 300 further includes mating the cable with the head at 306. The cable can be mated with the head prior to or after positioning the head within or entirely through interior portion of the bone at 302.

The method 300 also includes tensioning the cable to a measurable and adjustable tension at 308. The cable is tensioned while passing through the head. In some implementations, tensioning the cable at 308 draws the cable into mating engagement with the head, such that tensioning the cable causes the cable to mate with the head. Mating engagement with the head can be facilitated by an arm engagement feature of the cable. Furthermore, the method 300 includes deploying the head to frictionally engage the interior portion of the bone or an external surface of the bone at 310. In some implementations, tensioning the cable at 308 causes the head to deploy at 310 via mating engagement between the cable and the head. With the cable in tension, the method 300 includes crimping the cable to maintain the tension in the cable and maintain the deployment of the head at 312.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. A deployable anchor for bone fixation, comprising:
a head, positionable within or entirely through an interior portion of a bone and, while positioned within or entirely through the interior portion of the bone, deployable to frictionally engage the bone and fixate the head relative to the bone;

a cable, coupled to the head, wherein the cable is configured to be tensioned to a measurable and adjustable tension; and
a washer fixedly coupled with the head.

2. The deployable anchor according to claim 1, wherein the cable is coupled to the head such that tensioning of cable causes deployment of the head.

3. The deployable anchor according to claim 2, wherein:
the head comprises at least two arms, each comprising bone engagement features;
the cable comprises an arm engagement portion; and
the arm engagement portion of the cable causes the at least two arms to deform outwardly away from each other as the cable is tensioned.

4. The deployable anchor according to claim 1, wherein:
the head comprises at least two arms separated by slits; and
each of the at least two arms comprises bone engagement features extending outwardly away from each other.

5. The deployable anchor according to claim 4, wherein each of the at least two arms comprises a tapered interior surface.

6. The deployable anchor according to claim 4, wherein the bone engagement features comprise non-helical teeth.

7. The deployable anchor according to claim 4, wherein the bone engagement features comprise helical teeth.

8. The deployable anchor according to claim 1, further comprising an elongate shaft extending between the washer and the head.

9. The deployable anchor according to claim 8, wherein a distance between the washer and the head is adjustable.

10. The deployable anchor according to claim 9, further comprising a telescoping element movably coupled with the elongate shaft, wherein:
the washer is fixed to the telescoping element; and
the telescoping element is translationally movable relative to the elongate shaft to adjust the distance between the washer and the head.

11. The deployable anchor according to claim 10, further comprising a spring positioned within the elongate shaft between the telescoping element and the head.

12. The deployable anchor according to claim 8, further comprising bone engagement features between the washer and the elongate shaft, wherein when the head is positioned within or entirely through the interior portion of the bone, the bone engagement features frictionally engage a near cortex of the bone and the head is deployable to frictionally engage a far cortex of the bone.

13. The deployable anchor according to claim 8, further comprising:
external threads between the elongate shaft and the washer; and
a compression nut threadably engaged with the external threads such that rotation of the compression nut relative to the external threads translationally moves the compression nut relative to the head.

14. The deployable anchor according to claim 1, further comprising a central channel extending entirely through the head and the washer.

15. The deployable anchor according to claim 14, wherein the cable is passable through the central channel.

16. The deployable anchor according to claim 15, wherein movement of the cable along the central channel is constrained in a first direction and a second direction, opposite the first direction.

17. The deployable anchor according to claim 16, wherein:

the cable comprises a plug positioned within the central channel when the cable passes through the central channel;
the central channel comprises a stop configured to contact and prevent movement of the plug relative to the central channel in the first direction; and
the deployable anchor is insertable into the bone in the first direction and removable from the bone in the second direction.

18. A system for stabilizing a bone, the system comprising:
a deployable anchor, comprising:
a head, positionable within or entirely through an interior portion of a bone and, while positioned within or entirely through the interior portion of the bone, deployable to frictionally engage the bone and fixate the head relative to the bone; and
a cable, coupled to the head, wherein the cable is configured to be tensioned to a measurable and adjustable tension; and
a tensioner, configured to tension the cable to the measurable and adjustable tension.

19. The system according to claim 18, further comprising a fixation device positionable externally relative to the bone, wherein the fixation device is fixable to the bone via engagement with the cable.

20. The system according to claim 19, wherein:
the deployable anchor further comprises a washer fixedly coupled with the head;
the fixation device comprises a recess; and
the washer is one of nestably engaged or threadably engaged with the recess of the fixation device.

21. A method of anchoring cable to bone, the method comprising:
positioning a head within or entirely through an interior portion of a bone;
passing a cable through the head and coupling the cable to the head, wherein the cable is configured to be tensioned to a measurable and adjustable tension; and
while the head is positioned within or entirely through the interior portion of the bone, deploying the head to frictionally engage the bone and fixate the head relative to the bone; and
wherein a washer is fixedly coupled with the head.

22. The method according to claim 21, further comprising tensioning the cable to the measurable and adjustable tension, wherein tensioning the cable deploys the head.

23. The method according to claim 22, wherein:
the cable comprises an arm engagement portion;
the head comprises at least two arms, each comprising bone engagement features; and
deploying the head comprises moving the arm engagement portion of the cable along the at least two arms, as the cable is tensioned, to deform the at least two arms outwardly away from each other.

24. The method according to claim 22, further comprising crimping the cable, while tensioned to the measurable and adjustable tension, to maintain tension in the cable and deployment of the head.

25. The method according to claim 21, further comprising positioning a washer, coupled to the head, proximate a first surface of the bone, wherein the interior portion of the bone comprises a near cortex of the bone that defines the first surface of the bone.

26. The method according to claim 25, further comprising:

positioning a fixation device external to the first surface of the bone;

coupling the cable to the fixation device; and fixating the fixation device relative to the bone by tensioning the cable to the measurable and adjustable tension.

27. The method according to claim 21, further comprising positioning a washer, coupled to the head, proximate a first surface of the bone, wherein:

the interior portion of the bone comprises a far cortex of the bone that defines a second surface of the bone opposite the first surface of the bone;

an elongate shaft extends between and couples together the head and the washer; and the elongate shaft passes through a medullary cavity and a near cortex of the bone that defines the first surface of the bone.

28. A deployable anchor for bone fixation, comprising:

a head, positionable within or entirely through an interior portion of a bone and, while positioned within or entirely through the interior portion of the bone, deployable to frictionally engage the bone and fixate the head relative to the bone;

a rod coupled to the head;

a driver rotatably coupled with the rod, wherein rotation of the driver relative to the rod moves the rod relative to the head and deploys the head; and a washer fixedly coupled with the head.

* * * * *